United States Patent [19]
Fraley et al.

[11] Patent Number: 5,792,761
[45] Date of Patent: Aug. 11, 1998

[54] THROMBIN INHIBITORS

[75] Inventors: Mark E. Fraley, North Wales; Adel M. Naylor-Olsen; Randall W. Hungate, both of Lansdale; Joseph P. Vacca, Telford, all of Pa.

[73] Assignee: Merck & Co., Inc., Rahway, N.J.

[21] Appl. No.: 907,446

[22] Filed: Aug. 8, 1997

[51] Int. Cl.$^6$ .................. A61K 31/34; C07D 213/72; C07D 215/02; C07D 223/16
[52] U.S. Cl. .................. 514/212; 514/314; 514/337; 514/339; 514/352; 540/593; 546/165; 546/166; 546/277.4; 546/281.7; 546/282.7; 546/284.1; 546/304
[58] Field of Search .................. 514/212, 314, 514/337, 339, 352; 540/593; 546/165, 166, 277.4, 281.7, 282.7, 284.1, 304

[56] References Cited

U.S. PATENT DOCUMENTS

| | | | |
|---|---|---|---|
| 4,455,427 | 6/1984 | Johnson | 546/269 |
| 5,534,536 | 7/1996 | Ohuchida et al. | 514/397 |
| 5,594,004 | 1/1997 | Katano et al. | 514/301 |
| 5,602,253 | 2/1997 | Antonsson et al. | 544/330 |

FOREIGN PATENT DOCUMENTS

| | | |
|---|---|---|
| 195212 | 9/1986 | European Pat. Off. |
| 363284 | 4/1990 | European Pat. Off. |
| 601459 | 6/1994 | European Pat. Off. |

OTHER PUBLICATIONS

Edwards et al., Design, Synthesis, and Kinetic Evaluation of a Unique Class of Elastase Inhibitors, the piptidyl alpha–ketobenzoxazoles, J. Am. Chem. Soc., vol. 114, No. 1, pp. 1854–1863, 1992.

*Primary Examiner*—Mukund J. Shah
*Assistant Examiner*—Deepak R. Rao
*Attorney, Agent, or Firm*—Richard S. Parr; Mel Winokur

[57] ABSTRACT

A compound which inhibits human thrombin and where has the structure

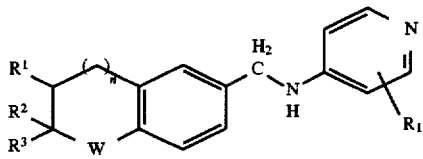

such as

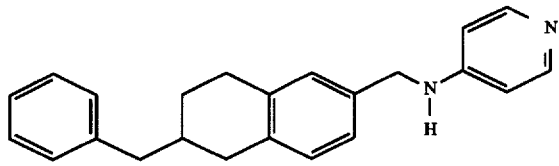

8 Claims, No Drawings

THROMBIN INHIBITORS

This application claims benefit from Provisional application Ser. No. 60/023,829 filed Aug. 12, 1996.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.* (1992) vol. 114, pp. 1854-63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or α-keto carboxyl derivatives.

Thrombin inhibitors described in prior publications contain sidechains of arginine and lysine. These structures show low selectivity for thrombin over other trypsin-like enzymes. Some of them show toxicity of hypotension and liver toxicity.

European Publication 601 459 describes sulfonamido heterocyclic thrombin inhibitors, such as N-[4-[(aminoimino-methyl)amino]butyl]-1-[N-(2-naphthalenylsulfonyl)-L-phenylalanyl]-L-prolinamide.

WO 94/29336 describes compounds which are useful as thrombin inhibitors.

SUMMARY OF THE INVENTION

Compounds of the invention have the following structure:

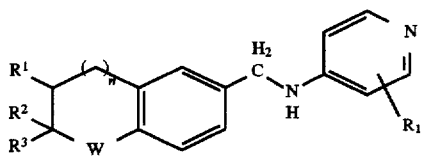

wherein
n=0, 1 or 2;
W=O, NH, or $CH_2$;
$R^1$=H,
  $C_{1-4}$ lower alkyl
  $C_{2-4}$ lower alkenyl,
  $C_{2-4}$ lower alkynyl;
$R^2$=
  —$C_6H_5$,
  —$C_6H_{11}$,
  —$(CH_2)_mC_6H_5$, or
  —$(CH_2)_mC_6H_{11}$,
where m=1 or 2; and
$R^3$=H,
  $C_{1-4}$ lower alkyl,
  $C_{2-4}$ lower alkenyl,
  $C_{2-4}$ lower alkynyl;
and pharmaceutically acceptable salts thereof.

These compounds show selectivity for thrombin inhibition over inhibition of trypsin and other trypsin-like enzymes. Trypsin-like enzymes (such as trypsin, thrombin, factor xa, kallikrein, plasmin, urokinase, and plasminogen activator) are serine dependent enzymes that catalyze hydrolysis at arginyl and lysyl peptide bonds.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes a composition for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

This invention also includes the use of a compound of the invention in the manufacture of a medicament for inhibiting thrombus formation, preventing thrombus formation, inhibiting thrombin, inhibiting formation of fibrin, and inhibiting formation of blood platelet aggregates in a mammal.

DETAILED DESCRIPTION OF THE INVENTION

Compounds of the invention have the following structure (formula I):

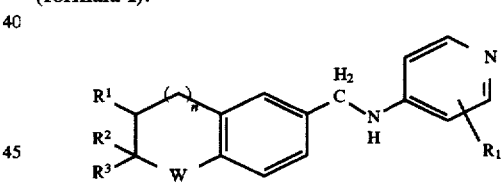

wherein
n=0, 1 or 2;
W=O, NH, or $CH_2$;
$R^1$=H,
  $C_{1-4}$ lower alkyl,
  $C_{2-4}$ lower alkenyl,
  $C_{2-4}$ lower alkynyl;
$R^2$=
  —$(CH_2)_mC_6H_5$, or
  —$(CH_2)_mC_6H_{11}$,
where m=0, 1 or 2; and
$R^3$=H,
  $C_{1-4}$ lower alkyl,
  $C_{2-4}$ lower alkenyl,
  $C_{2-4}$ lower alkynyl;
and pharmaceutically acceptable salts thereof.

A class of compounds of the invention have the following formula:

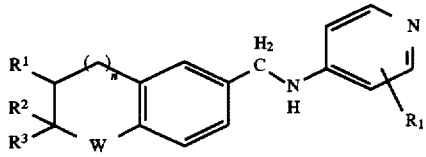

wherein n=1 or 2;

W=O or CH$_2$;

R$^1$=H or CH$_3$;

R$^2$=
—C$_6$H$_5$,
—C$_6$H$_{11}$,
—CH$_2$C$_6$H$_5$, or
—CH$_2$C$_6$H$_{11}$; and R$^3$=H or CH$_3$.

and pharmaceutically acceptable salts thereof.

Specific embodiments of the compounds include

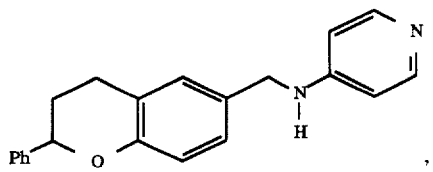

,

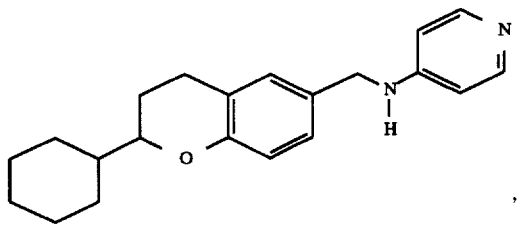

,

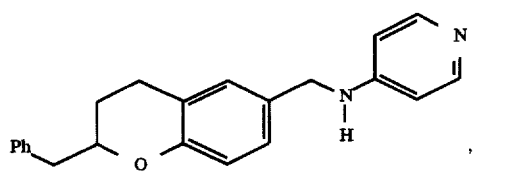

,

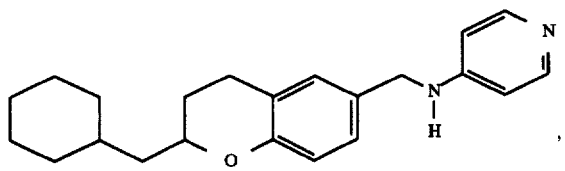

,

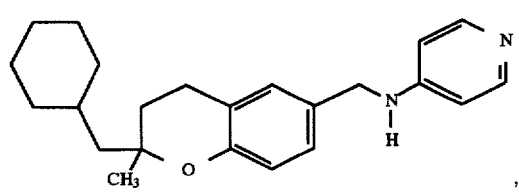

,

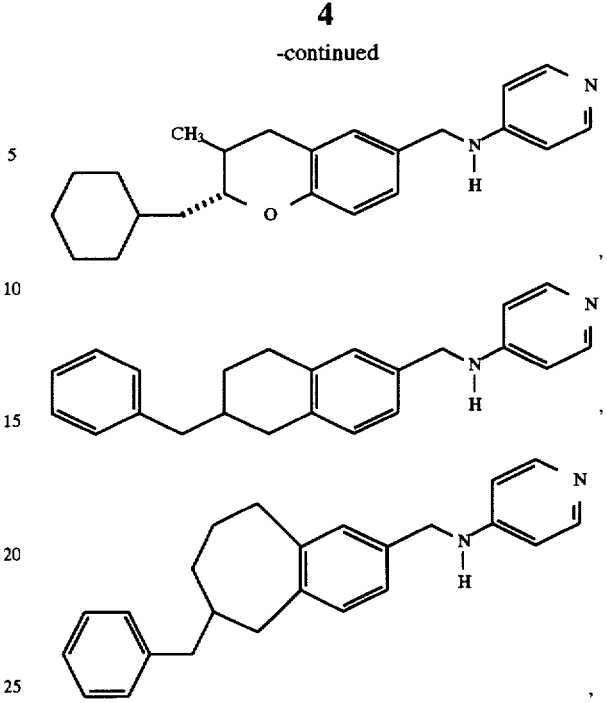

, and pharmaceutically acceptable salts thereof.

Some abbreviations that may appear in this application are as follows.

| Designation | |
|---|---|
| BOC (Boc) | t-butyloxycarbonyl |
| HBT(HOBT or HOBt) | 1-hydroxybenzotriazole hydrate |
| BBC reagent | benzotriazolyloxy-bis(pyrrolidino)-carbonium hexafluorophosphate |
| PyCIU | 1,1,3,3-bis(tetramethylene)-chlorouronium hexafluorophosphate |
| EDC | 1-ethyl-3-(3-dimethylaminopropyl) carbodiimide hydrochloride |
| (BOC)$_2$O | di-t-butyl dicarbonate |
| DMF | dimethylformamide |
| Et$_3$N or TEA | triethylamine |
| EtOAc | ethyl acetate |
| TFA | trifluoroacetic acid |
| DMAP | dimethylaminopyridine |
| DME | dimethoxyethane |
| BH3-THF | Borane-tetrahydrofuran complex |
| D-Phe(3,4-Cl$_2$) | D-3,4-Dichlorophenylalanine |
| D-3,3-dicha | D-3,3-Dicyclohexylalanine |
| Pro | Proline |
| Arg | Arginine |
| Gly | Glycine |
| D-3,3,-diphe | D-3,3-Diphenylalanine |
| LAH | lithium aluminum hydroxide |
| Cy | cyclohexyl |

The compounds of the present invention may have chiral centers and occur as racemates, racemic mixtures and as individual diastereomers, or enantiomers with all isomeric forms being included in the present invention.

The term "alkyl" means straight or branched alkane containing 1 to about 10 carbon atoms, e.g., methyl, ethyl, n-propyl, isopropyl, n-butyl, isobutyl, sec-butyl, tert-butyl, pentyl, iso-amyl, hexy, octyl radicals and the like. The term "alkenyl" means straight or branched alkene containing 2 to about 10 carbon atoms, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like. The term "alkynyl" means straight or branched alkyne containing 2 to about 10 carbon atoms, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others.

Compounds of the invention can be prepared according to the following general synthetic strategy: suitable starting materials such as 2-hydroxyacetophenone and an aldehyde are cyclized to give a benzopyranone, which is reduced to form the benzopyran

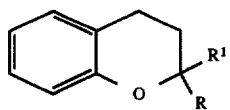

I where R is, for example, hydrogen or CH$_3$, and R$^1$ is, for example, phenyl, cyclohexyl, cyclohexylmethyl, or benzyl. The benzopyran is then oxidized with, for example, dimethylformamide and phosphorous oxychloride, and then further oxidized with, for example, sodium phosphate monobasic and sodium chlorite, to form

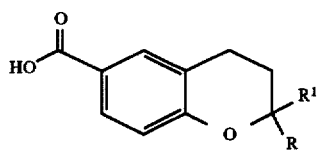

II which is coupled with 4-aminopyridine, or substituted 4-aminopyridine such as 4-amino-2-methylpyridine or 4-amino-3-methylpyridine, under standard amide coupling conditions to give

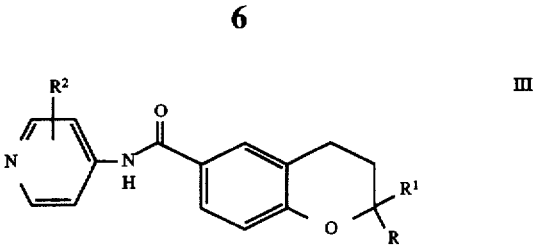

III (where R$^2$ is the substituent attached to 4-aminopyridine) which is reduced, for example with lithium aluminum hydride in tertahydrofuran, to form

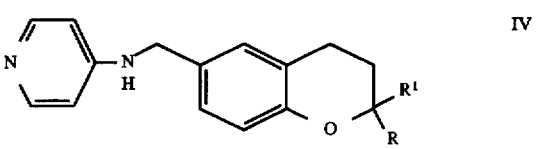

IV

EXAMPLE 1

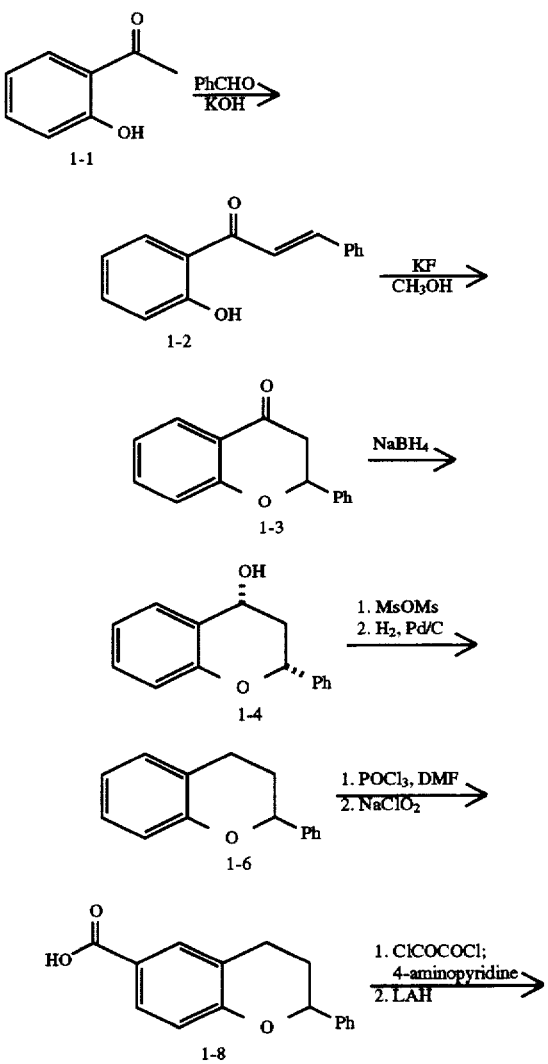

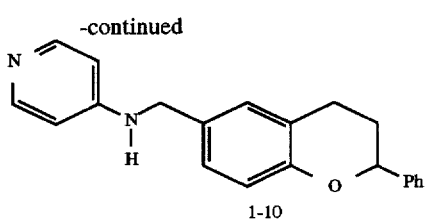

Preparation of 1-10

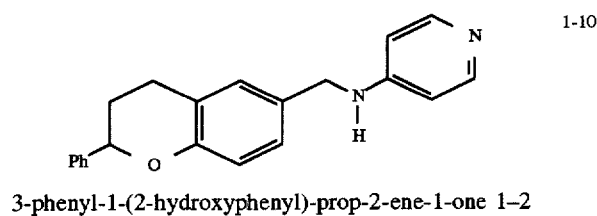

3-phenyl-1-(2-hydroxyphenyl)-prop-2-ene-1-one 1-2

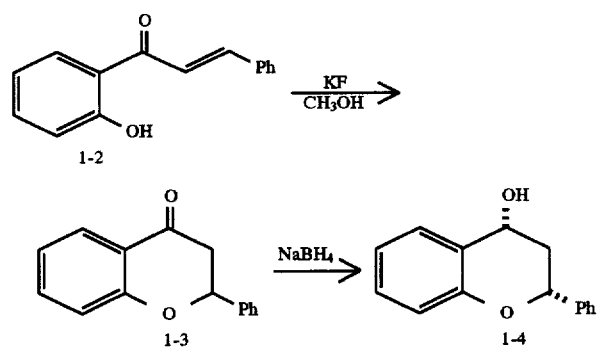

A solution of potassium hydroxide (70.0 g, 1.25 mol, 10.0 equiv) was added to a solution of benzaldehyde (16.5 mL, 0.162 mol, 1.30 equiv) and 2'-hydroxyacetophenone 1—1 (Aldrich) (15.0 mL, 0.125 mol, 1 equiv) in methanol (150 mL) at 23° C. The resultant red-colored solution was stirred at 23° C. for 1.5 h, over which time small amounts of yellow precipitate formed. The suspension was poured into an aqueous sulfuric acid solution (2 N, 1.0 L), and the yellow mass which precipitated from the mixture was filtered then air-dried, providing the enone as a bright yellow crystalline solid (mp=72°–75° C.). $^1$H NMR (300 MHz, CDCl$_3$), δ: 12.79 (s, 1H, ArOH), 7.91 (d, 1H, J=15.4 Hz, PhCH=CH), 7.91 (dd, 1H, J=8.1, 1.5 Hz, ArH [meta to OH, ortho to CO]), 7.65 (d, 1H, J=15.4 Hz, PhCH=CH), 7.65 (m, 2H, PhH), 7.49 (td, 1H, J=7.3, 1.5 Hz, ArH), 7.42 (m, 3H, PhH), 7.02 (dd, 1H, J=8.4, 1.1 Hz, ArH [ortho to OH]), 6.93 (td, 1H, J=7.3, 1.3 Hz, ArH);.TLC (10% ethyl acetate-hexanes), R$_f$: Product enone: 0.27 (visibly yellow)

Compound 1-4

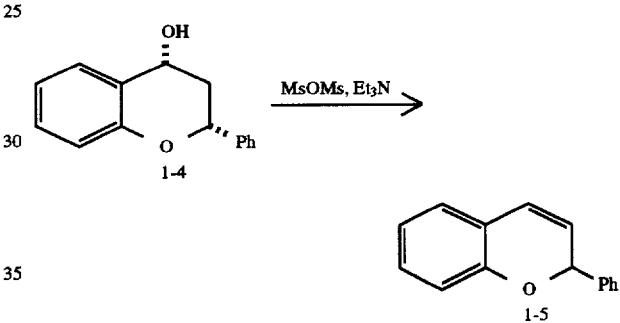

A suspension of the phenol 1-2 (10.0 g, 44.6 mmol, 1 equiv) and 50 wt. % potassium fluoride on Celite® (5.0 g, 43 mmol, 0.96 equiv) in methanol (150 mL) was heated at reflux for 3 h. After the suspension was allowed cool to 23° C., the solids were removed by filtration and washed with methanol (100 mL). The combined filtrate was concentrated to a volume of 100 mL, then cooled to 0° C. Sodium borohydride (3.0 g, 79 mmol, 1.8 equiv) was added, and the resultant mixture was warmed to 23° C. and stirred for 3 h. Excess sodium borohydride was quenched by the addition of acetone (5×2 mL) over a two-hour period. The mixture was concentrated to a volume of 15 mL, then diluted with water (500 mL). The aqueous mixture was extracted with two 200-mL portions of ethyl acetate. The combined organic layers were dried over sodium sulfate and were concentrated to afford the alcohol 1-4 as a colorless oil, which was used in the following step without further purification. $^1$H NMR (300 MHz, CDCl$_3$), δ: $^1$H NMR (300 MHz, CDCl$_3$), δ: 7.51 (br d, 1H, J=7.6 Hz, ArH), 7.46–7.34 (m, 5H, PhH), 7.21 (td, 1H, J=7.8, 1.7 Hz, ArH), 6.98 (1H, td, J=7.6, 1.0 Hz, ArH), 6.90 (dd, 1H, J=8.1, 1.0 Hz, ArH), 5.17 (dd, 1H, J=11.5, 1.7 Hz, OCHPh), 5.10 (ddd, 1H, J=10.5, 8.8, 6.1 Hz, CHOH), 2.51 (ddd, 1H, J=13.2, 6.1, 2.0 Hz, CH$_2$), 2.12 (ddd, 1H, J=13.2, 11.5, 10.8 Hz, CH$_2$), 1.83 (d, 1H, J×8.8 Hz, OH); TLC (40% ethyl acetate-hexanes), Product alcohol: R$_f$=0.33

Olefin 1-5

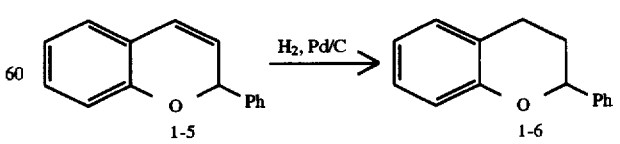

Methanesulfonic anhydride (1.80 g, 10.3 mmol, 1.17 equiv) was added to a solution of the alcohol 1-4 (2.00 g, 8.84 mmol, 1 equiv) and triethylamine (3.70 mL, 26.5 mmol, 3.00 equiv) in dichloromethane (50 mL) at 0° C. The reaction mixture was allowed to warm to 23° C., then stirred for 2.5 h. The solution was concentrated, and the residue was loaded onto a column of solvated (10% ethyl acetate in hexanes) flash-grade silica gel. Elution (10% ethyl acetate in hexanes) provided the dehydrated product 1-5 as a colorless oil. $^1$H NMR (400 MHz, CDCl$_3$), δ: 7.46 (m, 2H, PhH), 7.40–7.31 (m, 3H, PhH), 7.11 (td, 1H, J=7.6, 1.7 Hz, ArH), 7.01 (dd, 1H, J=7.5, 1.7 Hz, ArH), 6.86 (td, 1H, J=7.5, 1.1 Hz, ArH), 6.79 (br d, 1H, J=8.1 Hz, ArH), 6.53 (dd, 1H, J=9.8, 1.5 Hz, CH=CH), 5.92 (dd, 1H, J=3.2, 1.8 Hz, OCHPh), 5.80 (dd, 1H, J=9.8, 3.3 Hz, CH=CH); TLC (40% ethyl acetate-hexanes), Product: R$_f$=0.64

Compound 1-6

A suspension of the olefin 1-5 (350 mg, 1.68 mmol, 1 equiv) and 10% palladium on carbon (152 mg, 0.143 mmol, 0.085 equiv) in ethyl acetate (40 mL) was stirred at 23° C.

under a hydrogen balloon for 2 h. The catalyst was removed by filtration through a pad of Celite® and was washed with ethyl acetate (100 mL). The filtrate was concentrated to afford the benzopyran 1–6 as a colorless oil. $^1$H NMR (400 MHz, CDCl$_3$), δ: 7.45–7.30 (m, 5H, PhH), 7.12 (m, 2H, ArH), 6.89 (m, 2H, ArH), 5.07 (dd, 1H, J=10.0, 2.4 Hz, OCHPh), 3.00 (ddd, 1H, J=16.8, 11.2, 6.0 Hz, ArCH$_2$CH$_2$, 2.80 (ddd, 1H, J=16.8, 4.8, 3.8 Hz, ArCH$_2$CH$_2$), 2.23 (m, 1H, ArCH$_2$CH$_2$), 2.12 (m, 1H, ArCH$_2$CH$_2$); TLC (10% ethyl acetate-hexanes). Product benzopyran: R$_f$=0.40.

Aldehyde 1–7

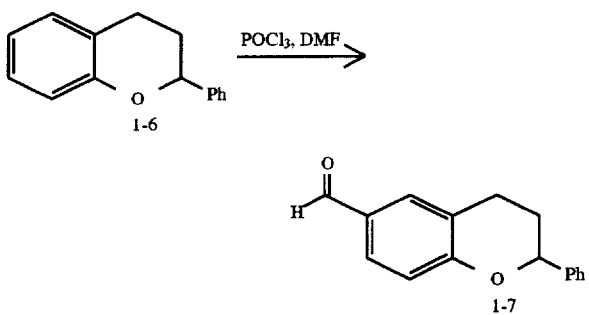

Phosphorus oxychloride (2.70 mL, 29.0 mmol, 10.2 equiv) was added dropwise over 1 min to N,N-dimethylformamide (2.30 mL, 29.7 mmol, 10.4 equiv) cooled to 0° C. The reaction mixture was allowed to warm to 23° C. and was stirred for 15 min. A solution of the benzopyran 1–6 (600 mg, 2.85 mmol, 1 equiv) in N,N-dimethyl-formamide (3 mL) was added to the reaction mixture. The resultant mixture was immersed in an oil bath preheated to 100° C. and held at that temperature for 6.25 h. The mixture was allowed to cool to 23° C., then poured into ice water (100 mL). The aqueous mixture was diluted with water (50 mL) and extracted with dichloromethane (3×50 mL). The combined organic layers were dried over sodium sulfate and were concentrated. The residue was purified by flash column chromatography (10% ethyl acetate in hexanes initially, grading to 30% ethyl acetate in hexanes) to afford the aldehyde 1–7 as a colorless oil. $^1$H NMR (400 MHz, CDCl$_3$), δ: 9.85 (s, 1H, CHO), 7.67 (br d, 1H, J=7.8 Hz, ArH), 7.65 (br s, 1H, ArH), 7.43–7.33 (m, 5H, PhH), 7.05 (d, 1H, J=7.8 Hz, ArH), 5.17 (dd, 1H, J=10.2, 2.6 Hz, OCHPh), 3.04 (ddd, 1H, J=16.6, 11.4, 5.8 Hz, ArCH$_2$CH$_2$), 2.73 (dt, 1H, J=16.6, 4.4 Hz, ArCH$_2$CH$_2$), 2.60 (m, 1H, ArCH$_2$CH$_2$), 2.13 (m, 1H, ArcH2CH$_2$); TLC (10% ethyl acetate-hexanes), Product aldehyde: R$_f$=0.09

Acid 1–8

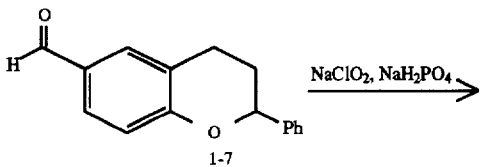

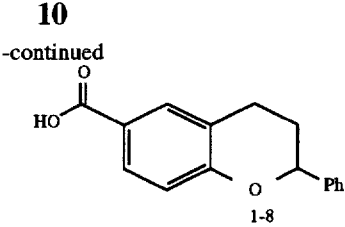

A solution of 80 wt. % sodium chlorite (114 mg, 1.01 mmol, 1.85 equiv) and sodium phosphate monobasic (116 mg, 0.841 mmol, 1.54 equiv) in water (2 mL) was added in two equal portions over 5 min to a solution of the aldehyde 1–7 (130 mg, 0.545 mmol, 1 equiv) and 2-methyl-2-butene (2M in THF, 1.00 mL, 2.00 mmol, 3.67 equiv) in tert-butanol (1 mL) at 23° C. After the reaction mixture was stirred for an additional 5 min, a solid mixture of 80 wt. % sodium chlorite (120 mg, 1.06 mmol, 1.95 equiv) and sodium phosphate monobasic (114 mg, 0.826 mmol, 1.52 equiv) was added in two equal portions over 10 min. The reaction mixture was stirred for an additional 25 min, then the volatiles were removed in vacuo. Ethyl acetate (20 mL) was added to the residue, and the resulting mixture was washed with an aqueous mixture of 10% sodium bisulfite solution (50 mL) and 10% potassium hydrogen sulfate solution (1 mL). The aqueous phase was extracted with ethyl acetate (2×30 mL), and the combined organic layers were dried over sodium sulfate and were concentrated to provide the carboxylic acid 1–8 as a white solid, which was used in the following step without further purification. TLC (40% ethyl acetate-hexanes). Product carboxylic acid: R$_f$=0.18 (UV).

Pyridine amide 1–9

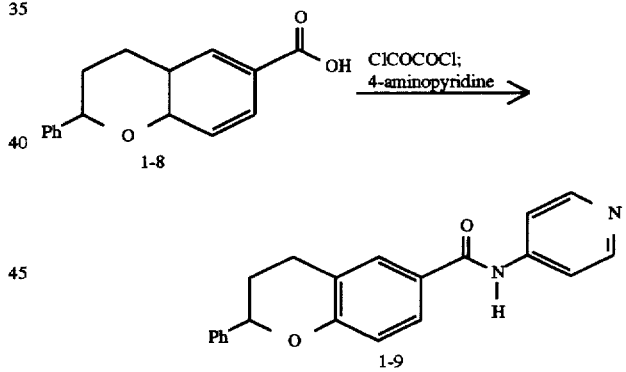

Oxalyl chloride (200 mL, 2.29 mmol, 4.20 equiv) and a catalytic amount of N,N-dimethylformamide (2 mL) were added consecutively to a suspension of the carboxylic acid 1–8 (150 mg, 0.545 mmol [corrected], 1 equiv) in dichloromethane (4 mL) at 23° C. Once gas evolution ceased (approximately 5 min following the addition of N,N-dimethylformamide), the volatiles were removed in vacuo. The residue was dissolved in dichloromethane (3 mL) and the resulting solution was transferred via cannula to a suspension of 4-aminopyridine (116 mg, 1.23 mmol, 2.26 equiv) and triethylamine (700 mL, 5.02 mmol, 9.21 equiv) in dichloromethane (3 mL) at 0° C. The reaction mixture was allowed to warm to 23° C., then was stirred for 1 h. The product mixture was loaded onto a column of solvated (ethyl acetate) flash-grade silica gel. Elution (ethyl acetate, initially, then 5% methanol in ethyl acetate) provided the product amide 1–9 as a white solid. $^1$H NMR (400 MHz, CDCl₃). δ: 8.53 (br d, 2H, J=6.4 Hz, PyH), 8.11 (br s, 1H, NH), 7.70 (br s, 1H, ArH), 7.64 (dd, 1H, J=8.6, 2.4 Hz, ArH), 7.61 (br d, 2H, J=6.4 Hz, PyH), 7.42-7.33 (m, 5H, PhH), 6.98 (d, 1H, J=8.6 Hz, ArH), 5.15 (dd, 1H, J=10.0, 2.4 Hz, OCHPh), 3.02 (ddd, 1H, J=16.8, 11.0, 5.8 Hz, ArCH₂CH₂), 2.85 (td, 1H, J=16.8, 4.6 Hz, ArCH₂CH₂), 2.27 (m, 1H, ArCH₂CH₂), 2.11 (m, 1H, ArCH₂CH₂); TLC (ethyl acetate), Product amide: R_f=0.12 (UV).

Aminopyridine 1-10

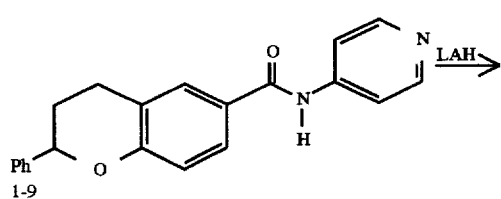

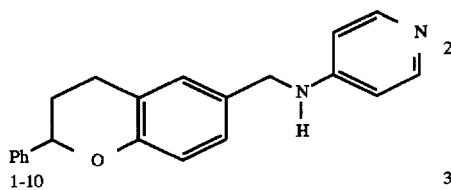

A solution of lithium aluminum hydride in tetrahydrofuran (1.0M, 1.00 mL, 1.00 mmol, 3.30 equiv) was added to a solution of the amide 1-9 (100 mg, 0.303 mmol, 1 equiv) in tetrahydrofuran (3 mL) at 0° C. The reaction mixture was warmed to 23° C. and stirred for 30 min, then heated to 50° C. for 45 min. The mixture was cooled to 0° C, and excess lithium aluminum hydride was quenched by the addition of water (20 mL). Aqueous 15% sodium hydroxide solution (60 mL) and water (20 mL) were added consecutively, and the resulting aluminum salts were removed by filtration and washed with ethyl acetate (50 mL). The filtrate was concentrated, and the residue was purified by flash column chromatography (1% methanol in chloroform saturated with ammonia) to afford the final product 1-10 as a white solid (mp=119°-122° C.). ¹H NMR (400 MHz, CDCl₃), δ: 8.20 (br d, 2H, J=6.4 Hz, PyH), 7.44-7.30 (m, 5H, PhH), 7.08 (br d, 1H, J=8.2 Hz, ArH), 7.05 (br s, 1H, ArH), 6.90 (d, 1H, J=8.2 Hz, ArH), 6.47 (br d, 2H, J=6.4 Hz, PyH), 5.06 (dd, 1H, J=10.1, 2.4 Hz, OCHPh), 4.51 (br s, 1H, NH), 4.25 (d, 2H, J=5.3 Hz, CH₂), 2.98 (ddd, 1H, J=16.8, 10.9, 6.0 Hz, ArCH₂CH₂), 2.77 (td, 1H, J=16.8, 4.6 Hz, ArCH₂CH₂), 2.22 (m, 1H, ArCH₂CH₂), 2.09 (m, 1H, ArCH₂CH₂); TLC (1% CH₃OH-CHCl₃ sat'd w/NH₃), R_f=0.20 (UV); Low-Res MS (FAB): Calcd for C₂₁H₂₁N₂O₁ [M+H]⁺: 317; Found: 317.

EXAMPLE 2

Preparation of 1,2,3,4-tetrahydro-2(RS)-cyclohexyl-6-(4'-amino-pyridyl)methyl-benzopyran 2-7

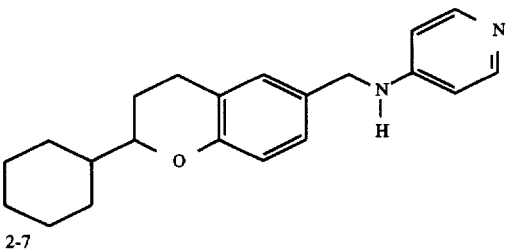

2,3-dihydro-2(RS)-cyclohexyl-benzopyran-4-one 2—2

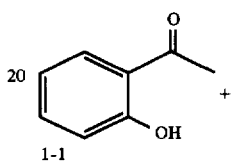

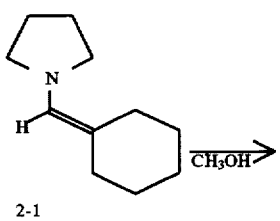

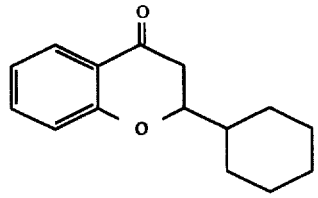

A solution of cyclohexanecarboxaldehyde (Aldrich) (5.40 mL, 446 mmol, 1 equiv) and pyrrolidine (8.60 mL, 103 mmol, 2.31 equiv) in benzene (30 mL) was heated at reflux with the azeotropic removal of water via a Dean-Stark apparatus for 16 h. After cooling to 23° C., the volatiles were removed in vacuo, and the residue was dissolved in anhydrous methanol (30 mL) giving 2-1. 1—1 (5.21 mL, 433 mmol, 0.970 equiv) was added and the resultant red-colored mixture was stirred at 23° C. for 16 h. The product mixture was concentrated and the residue was purified by flash column chromatography (⁵% ethyl acetate in hexanes) to provide the chromanone product 2-2 as a light brown oil. ¹H NMR (400 MHz, CDCl₃), δ: 7.87 (dd, 1H, J=7.7, 1.7 Hz, ArH), 7.46 (td, 1H, J=7.3, 1.8 Hz, ArH), 7.99 (br t, 1H, J=7.8 Hz, ArH), 6.97 (br d, 1H, J=8.4 Hz, ArH), 4.21 (m, 1H, OCH), 2.74 (dd, 1H, J=16.6, 12.4 Hz, C(O)CH₂), 2.66 (dd, 1H, J=16.7, 3.5 Hz, C(O)CH₂), 1.99 (br d, 1H, J=12.3 Hz, CyH), 1.87-1.68 (m, 5H, CyH), 1.38-1.10 (m, 5H, CyH); TLC (5% ethyl acetate-hexanes), R_f=0.18 (UV).

1,2,3,4-tetrahydro-2(RS)-cyclohexyl-benzopyran 2-3

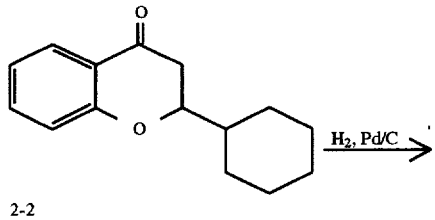

A suspension of the chromanone 2—2 (2.13 g, 9.25 mmol, 1 equiv) and 10% palladium on carbon (320 mg, 0.301 mmol, 0.0325 equiv) in acetic acid (20 mL) was heated at 70° C. under a hydrogen balloon for 16 h. After cooling to 23° C., the solids were removed by filtration through a pad of Celite® and were washed with ethyl acetate (100 mL). The filtrate was concentrated and the residue was purified by flash column chromatography (5% ethyl acetate in hexanes) to provide the benzopyran 2-3 as a colorless oil as well as recovered starting chromanone; $^1$H NMR (400 MHz, CDCl$_3$), δ: 7.09 (m, 2H, ArH), 6.85 (m, 2H, ArH), 3.78 (m, 1H, OCH), 2.83 (m, 2H, ArCH$_2$), 2.03 (m, 2H, ArCH$_2$CH$_2$ and CyH), 1.90–1.70 (m, 5H, ArCH$_2$CH$_2$ and CyH), 1.65 (m, 1H, CyH), 1.40–1.10 (m, 5H, CyH); TLC (5% ethyl acetate-hexanes), R$_f$=0.57 (UV).

1,2,3 4-tetrahydro-2(RS)-cyclohexyl-benzopyran-6-carboxaldehyde 2-4

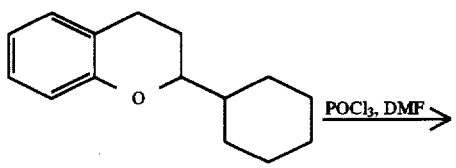

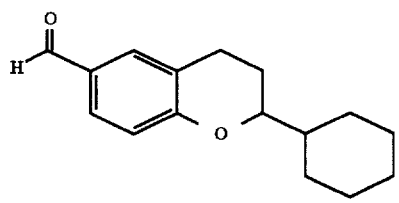

Phosphorus oxychloride (2.50 mL, 26.8 mmol, 5.00 equiv) was added slowly over 30 s to N,N-dimethylformamide (2.08 mL, 26.8 mmol, 5.00 equiv) cooled to 0° C. The reaction mixture was allowed to warm to 23° C. and was stirred for 15 min. A solution of the benzopyran 2-3 (1.16 g, 5.36 mmol, 1 equiv) in N,N-dimethyl-formamide (10 mL) was added to the reaction mixture. The resultant mixture was heated to 90° C. and held at that temperature for 1.5 h. The mixture was allowed to cool to 23° C., then poured into ice water (100 mL). The aqueous mixture was extracted with dichloromethane (2×100 mL). The combined organic layers were dried over magnesium sulfate and were concentrated. The residue was purified by flash column chromatography (10% ethyl acetate in hexanes) to afford the aldehyde 2-4 as a yellow solid. $^1$H NMR (400 MHz, CDCl$_3$), δ: 9.82 (s, 1H, CHO), 7.61 (br d, 1H, J=8.4 Hz, ArH), 7.59 (br s, 1H, ArH), 6.89 (d, 1H, J=8.2 Hz, ArH) 3.84 (m, 1H, OCH), 2.84 (m, 2H, ArCH$_2$), 2.01 (m, 2H, ArCH$_2$CH$_2$ and CyH), 1.85–1.68 (m, 5H, ArCH$_2$CH$_2$ and CyH), 1.63 (m, 1H, CyH), 1.36–1.10 (m, 5H, CyH); TLC (10% ethyl acetate-hexanes), R$_f$=0.54 (UV).

1,2,3 ,4-tetrahydro-2(RS)-cyclohexyl-benzopyran-6-carboxylic acid 2–5

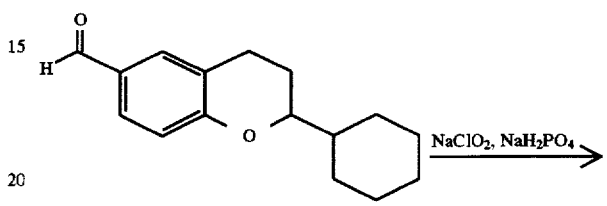

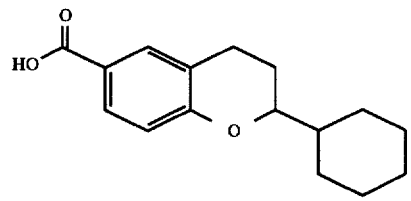

A solution of 80 wt. % sodium chlorite (45 mg, 0.50 mmol, 0.60 equiv) and sodium phosphate monobasic (68 mg, 0.50 mmol, 0.60 equiv) in water (3 mL) was added to a solution of the aldehyde 2–4 (203 mg, 0.832 mmol, 1 equiv) in a mixture of tert-butanol (4 mL) and 2-methyl-2-butene (1 mL) at 23° C. After the reaction mixture was stirred for 30 min, a solution of 80 wt. % sodium chlorite (75 mg, 0.83 mmol, 1.0 equiv) and sodium phosphate monobasic (114 mg, 0.826 mmol, 0.993 equiv) in water (5 mL) was added. The reaction mixture was stirred for 25 min, then the volatiles were removed in vacuo. Ethyl acetate (50 mL) was added to the residue, and the resulting solution was washed (2×) with an aqueous mixture of 10% sodium bisulfite solution (20 mL) and 10% potassium hydrogen sulfate solution (1 mL). The organic layer was dried over magnesium sulfate and was concentrated to provide the carboxylic acid 2–5 as a white solid, which was used in the following step without further purification.

N-4-pyridyl-(1,2,3,4-tetrahydro-2(RS)-cyclohexyl-benzopyran)-6 carboxamide 2–6

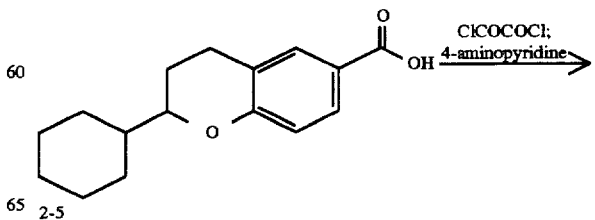

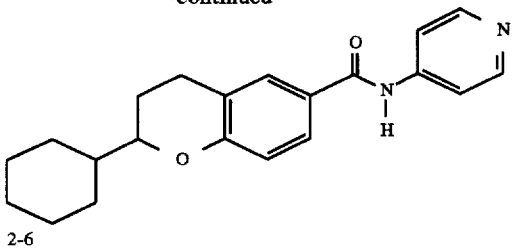

2-6

Oxalyl chloride (54 mL, 0.62 mmol, 3.0 equiv) was added to a suspension of the carboxylic acid 2–5 (54 mg, 0.21 mmol, 1 equiv) in dichloromethane (3 mL) at 23° C. Once gas evolution ceased (approximately 5 min following the addition), the volatiles were removed in vacuo. The residue was dissolved in dichloromethane (2 mL), and the resulting solution was transferred via cannula to a suspension of 4-aminopyridine (97 mg, 1.0 mmol, 5.0 equiv) and triethylamine (230 mL, 1.65 mmol, 7.97 equiv) in dichloromethane (2 mL) at 0° C. The reaction mixture was allowed to warm to 23° C., then was stirred for 2 h. The product mixture was concentrated, and the residue was purified by flash column chromatography (ethyl acetate) to provide the product amide 2–6 as a white solid. $^1$H NMR (400 MHz, CDCl$_3$), δ: 8.50 (br m, 2H, PyH), 7.83 (br s, 1H, NH), 7.58 (br s, 1H, ArH), 7.55 (br m, 3H, PyH and ArH), 6.83 (d, 1H, J=8.4 Hz, ArH), 3.80 (m, 1H, OCH), 2.81 (m, 2H, ArCH$_2$), 1.98 (m, 2H, ArCH$_2$CH$_2$ and CyH), 1.83–1.55 (m, 6H, ArCH$_2$CH$_2$ and CyH), 1.32–1.05 (m, 5H, CyH); TLC (ethyl acetate), R$_f$: Product amide: 0.30 (UV)

1,2,3,4-tetrahydro-2(RS)-cyclohexyl-6-(4'-aminopyridyl)methyl-benzopyran, 2–7

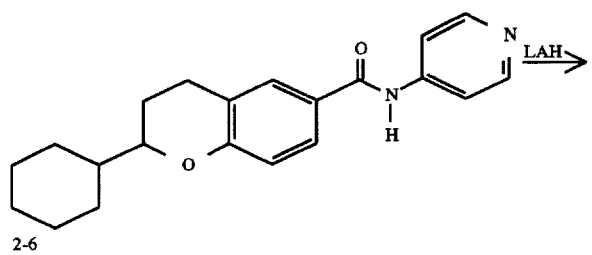

2-6

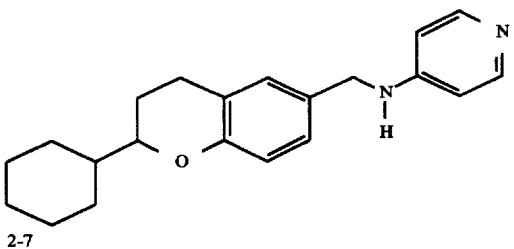

2-7

A solution of lithium aluminum hydride in tetrahydrofuran (1.0M, 640 mL, 0.640 mmol, 3.98 equiv) was added to a solution of the amide 2–6 (54 mg, 0.161 mmol, 1 equiv) in tetrahydrofuran (1 mL) at 23° C. The reaction mixture was heated to 50° C. and held at that temperature for 1.5 h. The mixture was cooled to 0° C., and excess lithium aluminum hydride was quenched by the addition of water (30 mL). Aqueous 15% sodium hydroxide solution (30 mL) and water (90 mL) were added consecutively, and the resulting aluminum salts were removed by filtration and washed with ethyl acetate (50 mL). The filtrate was concentrated and the residue was purified by flash column chromatography (1 % methanol in chloroform saturated with ammonia) to afford 2–7 as a white solid (mp=163°–165° C.); $^1$H NMR (400 MHz, CDCl$_3$), δ: 8.14 (br d, 2H, J=5.7 Hz, PyH), 6.98 (br d, 1H, J=8.2 Hz, ArH), 6.95 (br s, 1H, ArH), 6.73 (d, 1H, J=8.2 Hz, ArH), 6.41 (br d, 2H, J=5.7 Hz, PyH), 4.40 (br s, 1H, NH), 4.17 (d, 2H, J=5.1 Hz, CH$_2$), 3.69 (m, 1H, OCH), 2.72 (m, 2H, ArCH$_2$), 1.93 (m, 2H, ArCH$_2$CH$_2$ and CyH), 1.79–1.62 (m, 5H, ArCH$_2$CH$_2$ and CyH), 1.55 (m, 1H, CyH), 1.30–1.02 (m, 5H, CyH); Low-Res MS (FAB): Calcd for C$_{21}$H27N$_2$O$_1$ [M+H]$^+$: 323; Found: 323 TLC (1% CH$_3$OH-CHCl$_3$ sat'd w/NH$_3$), R$_f$ 0.33 (UV)

EXAMPLE 3

Preparation of 1,2,3,4-tetrahydro-2(RS)-benzyl-6-(4'-amino-pyridyl)methyl-benzopyran 3–8

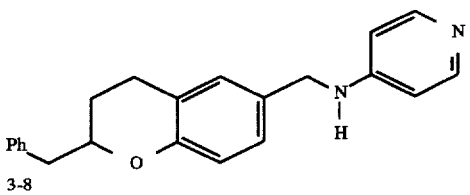

3-8

Alcohol 3–2

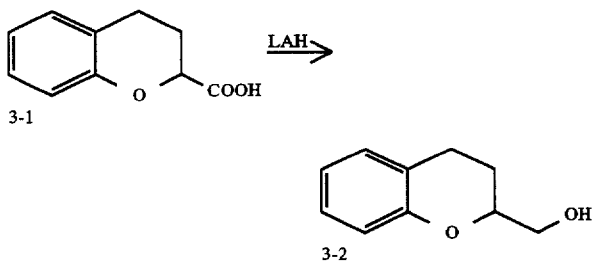

3-1

3-2

A solution of lithium aluminum hydride in tetrahydrofuran (1.0M, 84.0 mL, 84.0 mmol, 3.98 equiv) was added to a solution of the carboxylic acid 3–1 (J. Chem. Soc. Perkin Trans. 1 (1987) p. 2597; J. Med. Chem. (1972) vol. 15, p. 583; J. Med. Chem. (1968) vol. 11, p. 844) (3.76 g, 21.1 mmol, 1 equiv) in tetrahydrofuran (10 mL) at –78° C. The reaction mixture was stirred at –78° C. for 1 h, then warmed to 0° C. and held at that temperature for 2 h. Excess lithium aluminum hydride was quenched by the addition of water (3.0 mL). Aqueous 15% sodium hydroxide solution (3.0 mL) and water (9.0 mL) were added consecutively, and the resulting aluminum salts were removed by filtration and washed with ethyl acetate (100 mL). The filtrate was concentrated and the residue was purified by flash column chromatography (20% ethyl acetate in hexanes) to afford the alcohol 3–2 as a colorless oil. $^1$H NMR (400 MHz, CDCl$_3$), δ: 7.06 (m, 2H, ArH), 6.83 (m, 2H, ArH), 4.12 (m, 1H, OCH), 3.83 (m, 1H, CH$_2$OH), 3.76 (m, 1H, CH$_2$OH), 2.89 (ddd, 1H, J=17.2, 11.0, 5.5 Hz, ArCH$_2$CH$_2$), 2.77 (br d, 1H, J=16.7, ArCH$_2$CH$_2$), 2.11 (br s, 1H, OH), 1.95 (m, 1H, ArCH$_2$CH$_2$), 1.87 (m, 1H, ArCH$_2$CH$_2$); TLC (30% ethyl acetate-hexanes), R$_f$ Product alcohol: 0.53 (UV)

Compound 3-3

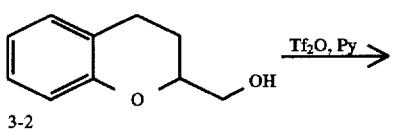

A solution of trifluoromethanesulfonic anhydride (1.73 mL, 10.3 mmol, 1.20 equiv) in dichloromethane (5 mL) was added dropwise over 2 min to a solution of the alcohol 3-2 (1.41 g, 8.59 mmol, 1 equiv) and pyridine (1.63 mL, 20.2 mmol, 2.35 equiv) in dichloromethane (35 mL) at –5° C. (ice-salt bath). The solution was allowed to warm to 0° C. and held at that temperature for 1 h. The reaction mixture was washed in sequence with water (20 mL), aqueous hydrochloric acid solution (1 N, 30 mL), water (30 mL), aqueous saturated sodium bicarbonate solution (30 mL), and water (30 mL). The organic layer was dried over magnesium sulfate and concentrated to afford the triflate 3—3 as a red-brown oil, which was used immediately in the following step without further purification. $^1$H NMR (400 MHz, CDCl$_3$), δ: 7.10 (m, 2H, ArH), 6.88 (m, 2H, ArH), 4.66 (m, 2H, CH$_2$OTf), 4.34 (m, 1H, OCH), 2.93 (ddd, 1H, J=16.6, 11.0, 5.4 Hz, ArCH$_2$CH$_2$), 2.82 (ddd, 1H, J=16.7, 5.9, 3.2 Hz, ArCH$_2$CH$_2$), 2.07 (m, 1H, ArCH$_2$CH$_2$), 1.90 (m, 1H, ArCH$_2$CH$_2$); TLC (20% ethyl acetate-hexanes), R$_f$ Product triflate: 0.70 (UV)

Compound 3-4

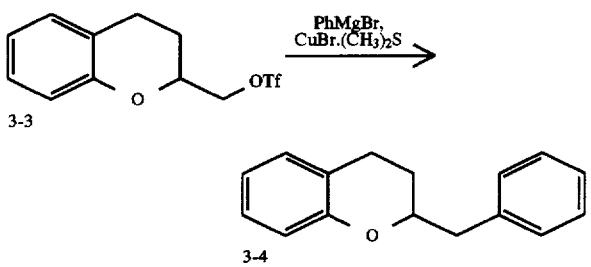

Copper(I) bromide-dimethyl sulfide complex (307 mg, 1.49 mmol, 0.174 equiv) was added to a solution of the unpurified triflate 3—3 (8.59 mmol) in tetrahydrofuran (35 mL) at –5° C. (ice-salt bath). A solution of phenylmagnesium bromide in diethyl ether (3.0M, 7.86 mL, 23.6 mmol, 2.75 equiv) was added dropwise over 5 min to the resultant light-brown slurry. The reaction mixture was stirred at –5° C. for 2 h, then poured into a biphasic mixture of aqueous 15% ammonium chloride solution (70 mL) and dichloromethane (35 mL). The organic layer was separated and washed with aqueous saturated ammonium chloride solution (3×50 mL). The combined aqueous layers were extracted with dichlormethane (2×100 mL). The combined organic layers were dried over magnesium sulfate and were concentrated. The residue was purified by flash column chromatography (100% hexanes initially, then 30% ethyl acetate in hexanes) to furnish the desired benzopyran 3-4 as a light brown oil. $^1$H NMR (400 MHz, CDCl$_3$), δ: 7.35–7.21 (m, 5H, PhH), 7.06 (m, 2H, ArH), 6.82 (m, 2H, ArH), 4.22 (m, 1H, OCHBn), 3.15 (dd, 1H, J=13.7, 6.1 Hz, CH$_2$Ph), 2.87 (dd, 1H, J=13.7, 7.1 Hz, CH$_2$Ph), 2.77 (m, 2H, ArCH$_2$CH$_2$), 1.99 (m, 1H, ArCH$_2$CH$_2$), 1.71 (m, 1H, ArCH$_2$CH$_2$); TLC (10% ethyl acetate-hexanes), R$_f$ Product benzopyran: 0.74 (UV)

Compound 3-5

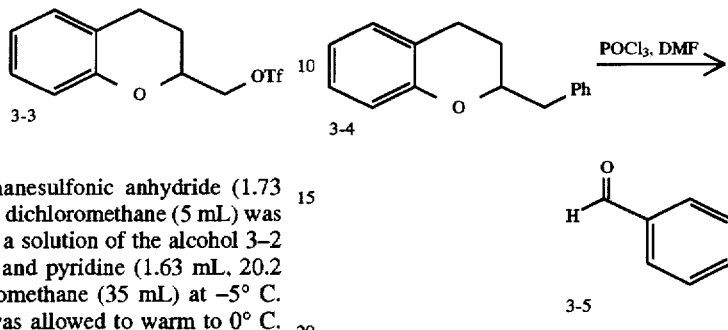

Phosphorus oxychloride (2.76 mL, 29.6 mmol, 5.00 equiv) was added slowly over 30 s to N,N-dimethylformamide (2.30 mL, 29.6 mmol, 5.00 equiv) cooled to 0° C. The reaction mixture was allowed to warm to 23° C. and was stirred for 15 min. A solution of the benzopyran 3-4 (1.33 g, 5.93 mmol, 1 equiv) in N,N-dimethylformamide (9 mL) was added to the reaction mixture. The resultant mixture was heated to 100° C. and held at that temperature for 3 h. The mixture was allowed to cool to 23° C., then poured into ice water (100 mL). The aqueous mixture was extracted with dichloromethane (3×50 mL). The combined organic layers were dried over magnesium sulfate and were concentrated. The residue was purified by flash column chromatography (5% ethyl acetate in hexanes initially, grading to 20% ethyl acetate in hexanes) to afford the aldehyde 3-5 as a yellow oil. $^1$H NMR (400 MHz, CDCl$_3$), δ: 9.83 (s, 1H, CHO), 7.62 (br d, 1H J=8.3 Hz, ArH), 7.60 (br s, 1H, ArH), 7.38–7.23 (m, 5H, PhH), 6.91 (d, 1H, J=8.3 Hz, ArH), 4.31 (m, 1H, OCHBn), 3.16 (dd, 1H, J=13.7, 6.4 Hz, CH$_2$Ph), 2.92 (dd, 1H, J=13.7, 6.8 Hz, CH$_2$Ph), 2.82 (m, 2H, ArCH$_2$CH$_2$), 2.06 (m, 1H, ArCH$_2$CH$_2$), 1.73 (m, 1H, ArCH$_2$CH$_2$); TLC (10% ethyl acetate-hexanes), R$_f$ Product aldehyde: 0.24 (UV)

Compound 3-6

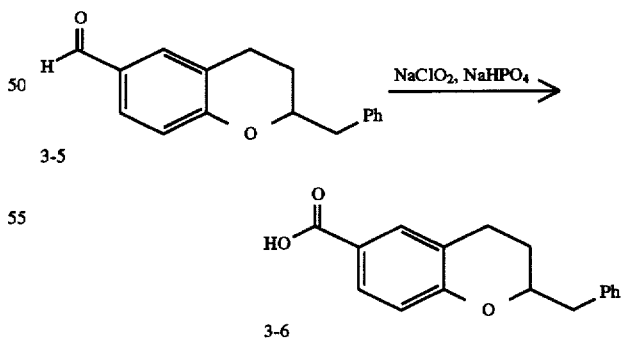

A solution of sodium phosphate monobasic (246 mg, 1.78 mmol, 2.00 equiv) in water (2 mL) and solid 80 wt. % sodium chlorite (161 mg, 1.78 mmol, 2.00 equiv) were added sequentially to a solution of the aldehyde 3-5 (225 mg, 0.892 mmol, 1 equiv) in a mixture of tert-butanol (4 mL) and 2-methyl-2-butene (1 mL) at 23° C. After the reaction mixture was stirred for 1 h, a mixture of 80 wt. % sodium chlorite (161 mg, 1.78 mmol, 2.00 equiv) and sodium phosphate monobasic (246 mg, 1.78 mmol, 2.00 equiv) were added in two equal portions with a 15 min interval between additions. The reaction mixture was stirred for an additional 15 min, then the volatiles were removed in vacuo. Ethyl acetate (75 mL) was added to the residue, and the resulting solution was washed (2×) with an aqueous mixture of 10% sodium bisulfite solution (24 mL) and 10% potassium hydrogen sulfate solution (1 mL). The organic layer was dried over magnesium sulfate and was concentrated to provide the carboxylic acid 3–6 as a white solid, which was used in the following step without further purification.

Compound 3-7

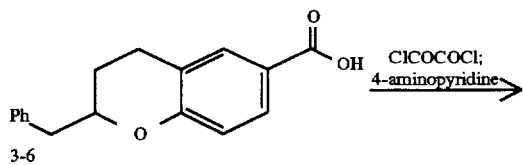

Oxalyl chloride (230 mL, 2.64 mmol, 3.01 equiv) was added to a suspension of the carboxylic acid 3–6 (235 mg, 0.876 mmol, 1 equiv) in dichloromethane (3 mL) at 23° C. Once gas evolution ceased (approximately 5 min following the addition), the volatiles were removed in vacuo. The residue was dissolved in dichloromethane (4 mL), and the resulting solution was transferred via cannula to a suspension of 4-aminopyridine (412 mg, 4.38 mmol, 5.00 equiv) and triethylamine (980 mL, 7.03 mmol, 8.03 equiv) in dichloromethane (2 mL) at 23° C. After the reaction mixture was stirred for 2.5 h, the volatiles were removed in vacuo. The residue was purified by flash column chromatography (ethyl acetate) to provide the product amide 3–7 as a white solid. $^1$H NMR (400 MHz, CDCl$_3$), δ: 8.50 (br d, 2H, J=5.4 Hz, PyH), 8.06 (br s, 1H, NH), 7.61 (br s, 1H, ArH), 7.59 (m, 3H, ArH and PyH), 7.35–7.23 (m, 5H, PhH), 6.86 (d, 1H, J=8.4 Hz, ArH), 4.28 (m, 1 H, OCHBn), 3.15 (dd, 1 H, J=13.7, 6.2 Hz, CH$_2$Ph), 2.91 (dd, 1H, J=13.7, 6.8 Hz, CH$_2$Ph), 2.80 (m, 2H, ArCH$_2$CH$_2$), 2.04 (m, 1H, ArCH$_2$CH$_2$), 1.73 (m, 1H, ArCH$_2$CH$_2$); TLC (ethyl acetate), R$_f$ Product amide: 0.24 (UV).

Compound 3-8

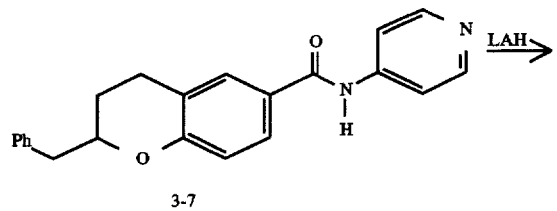

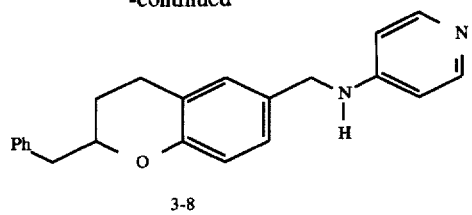

A solution of lithium aluminum hydride in tetrahydrofuran (1.0M, 2.43 mL, 2.43 mmol, 4.00 equiv) was added to a solution of the amide 3–7 (209 mg, 0.607 mmol, 1 equiv) in tetrahydrofuran (2 mL) at 23° C. The reaction mixture was heated to 50° C. and held at that temperature for 2 h. The mixture was cooled to 0° C., and excess lithium aluminum hydride was quenched by the addition of water (95 mL). Aqueous 15% sodium hydroxide solution (95 mL) and water (285 mL) were added consecutively, and the resulting aluminum salts were removed by filtration and washed with ethyl acetate (50 mL). The filtrate was concentrated and the residue was purified by flash column chromatography (1% methanol in chloroform saturated with ammonia) to afford 3–8 as a white foam. $^1$H NMR (400 MHz, CDCl$_3$), δ: 8.20 (br d, 2H, J=4.8 Hz, PyH), 7.35–7.22 (m, 5H, PhH), 7.05 (br d, 1H, J=8.2 Hz, ArH), 7.00 (br s, 1H, ArH), 6.80 (d, 1H J=8.2 Hz, ArH), 6.46 (br d, 2H, J=4.8 Hz, PyH), 4.39 (br s, 1H, NH), 4.23 (m, 3H, CH$_2$NH and OCHBn), 3.15 (dd, 1H, J=13.7, 6.2 Hz, CH$_2$Ph), 2.88 (dd, 1H, J=13.7, 6.9 Hz, CH$_2$Ph), 2.77 (m, 2H, ArCH$_2$CH$_2$), 2.00 (m, 1H, ArCH$_2$CH$_2$), 1.71 (m, 1H, ArCH$_2$CH$_2$); Low-Res MS (FAB): Calcd for C$_{22}$H23N$_2$O$_1$ [M+H]$^+$: 331 Found: 331; TLC (1% CH$_3$OH-CHCl$_3$ sat'd w/NH$_3$), R$_f$0.27 (UV)

EXAMPLE 4

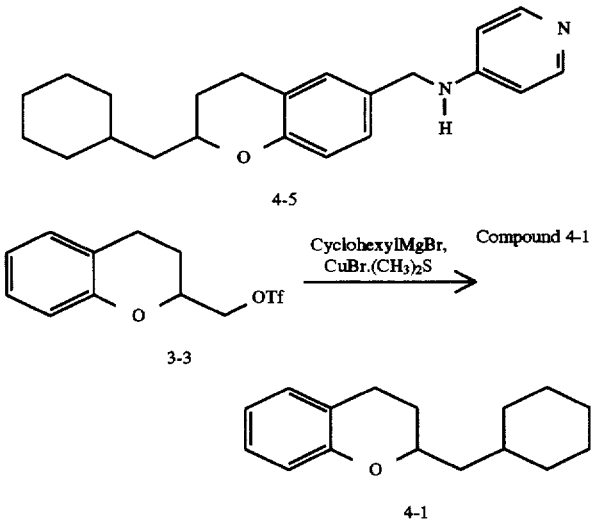

Using the procedure outlined in *J. Heterocyclic Chem.* (1992) vol. 29 p. 431, copper(I) bromide-dimethyl sulfide complex (104 mg, 0.505 mmol, 0.173 equiv) was added to a solution of the unpurified triflate 3—3 (867 mg, 2.92 mmol, 1 equiv) in tetrahydrofuran (10 mL) at –5° C. (ice-salt bath). A solution of cyclohexylmagnesium chloride in diethyl ether (2.0M, 3.95 mL, 7.90 mmol, 2.71 equiv) was added dropwise over 5 min to the resultant light-brown slurry. The reaction mixture was stirred at –5° C. for 1 h, then warmed to 0° C. and held at that temperature for 2 h. The reaction mixture was poured into a biphasic mixture of aqueous saturated ammonium chloride solution (20 mL) and dichloromethane (20 mL). The organic layer was separated and washed with aqueous saturated ammonium chloride solution (25 mL). The combined aqueous layers were extracted with dichlormethane (2×100 mL). The organic layer was dried over magnesium sulfate and were concentrated. The residue was purified by flash column chromatography (1% ethyl acetate in hexanes) to furnish the desired benzopyran 4–1 as a colorless oil. $^1$H NMR (400 MHz, CDCl$_3$), δ: 7.06 (m, 2H, ArH), 6.82 (m, 2H, ArH), 4.10 (m, 1H, OCHCH$_2$Cy), 2.86 (ddd, 1H, J=16.8, 11.0, 6.0 Hz, ArCH$_2$CH$_2$), 2.77 (dt, 1H, J=16.7, 3.8 Hz, ArCH$_2$CH$_2$), 1.98 (m, 1H, ArCH$_2$CH$_2$), 1.83 (br d, 1H, J=12.6 Hz, CyH), 1.80–1.55 (m, 6H, CyH, ArCH$_2$CH$_2$, and CH$_2$Cy), 1.42 (m, 1H, CyH), 1.36–1.13 (m, 4H, CyH), 0.97 (m, 2H, CyH); TLC (10% ethyl acetate-hexanes), R$_f$ Product benzopyran: 0.76 (UV).

Compound 4–2

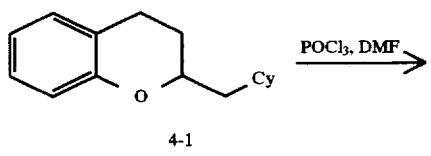

4-1

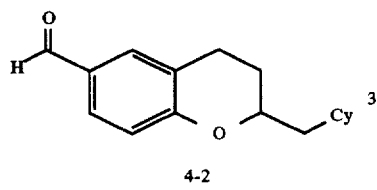

4-2

Phosphorus oxychloride (748 mL, 8.02 mmol, 5.00 equiv) was added slowly over 30 s to N,N-dimethylformamide (622 mL, 8.03 mmol, 5.00 equiv) cooled to 0° C. The reaction mixture was allowed to warm to 23° C. and was stirred for 15 min. A solution of the benzo-pyran 4–1 (370 mg, 1.61 mmol, 1 equiv) (where "Cy" represents the cyclohexyl moiety) in N,N-dimethylformamide (6 mL) was added to the reaction mixture. The resultant mixture was heated to 100° C. and held at that temperature for 2 h. The mixture was allowed to cool to 23° C., then poured into ice water (100 mL). The aqueous mixture was extracted with dichloromethane (2×75 mL). The combined organic layers were dried over magnesium sulfate and were concentrated. The residue was purified by flash column chromatography (1% ethyl acetate in hexanes initially, grading to 5% ethyl acetate in hexanes) to afford the aldehyde 4–2 as a colorless oil. $^1$H NMR (400 MHz, CDCl$_3$), δ: 9.83 (s, 1H, COH), 7.62 (br d, 1H, J=8.2 Hz, ArH), 7.60 (br s, 1H, ArH), 6.90 (d, 1H, J=8.4 Hz, ArH), 4.20 (m, 1H, OCHCH$_2$Cy), 2.86 (m, 2H, ArCH$_2$CH$_2$), 2.04 (m, 1H, ArCH$_2$CH$_2$), 1.83 (br d, 1H, J=12.6 Hz, CyH), 1.79–1.57 (m, 6H, CyH, ArCH$_2$CH$_2$, and CH$_2$Cy), 1.43 (m, 1H, CyH), 1.36–1.13 (m, 4H, CyH), 0.97 (m, 2H, CyH); TLC (5% ethyl acetate-hexanes), R$_f$ Product aldehyde: 0.15 (UV).

Compound 4–3

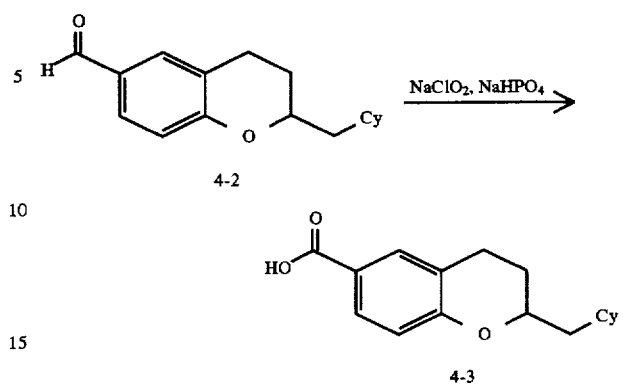

A solution of sodium phosphate monobasic (66 mg, 0.48 mmol, 2.0 equiv) in water (1 mL) and solid 80 wt. % sodium chlorite (43 mg, 0.48 mmol, 2.0 equiv) were added sequentially to a solution of the aldehyde 4–2 (62 mg, 0.24 mmol, 1 equiv) in a mixture of tert-butanol (4 mL) and 2-methyl-2-butene (1 mL) at 23° C. After the reaction mixture was stirred for 2.5 h, the volatiles were removed in vacuo. Ethyl acetate (25 mL) was added to the residue, and the resulting solution was washed (2 ×) with an aqueous mixture of 10% sodium bisulfite solution (24 mL) and 10% potassium hydrogen sulfate solution (1 mL). The organic layer was dried over magnesium sulfate and was concentrated to provide the carboxylic acid 4–3 as a white solid (>100%), which was used in the following step without further purification.

Compound 4—4

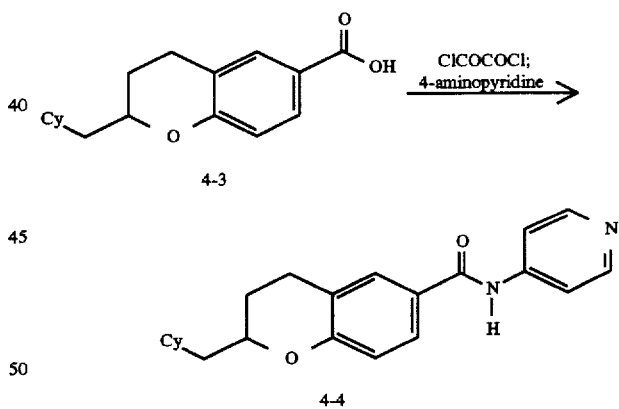

Oxalyl chloride (63 mL, 0.72 mmol, 3.0 equiv) and a catalytic amount of N,N-dimethylformamide (2 mL) were added sequentially to a suspension of the carboxylic acid 4–3 (0.24 mmol, 1 equiv) in dichloromethane (2 mL) at 23° C. Once gas evolution ceased (approximately 5 min following the addition of N,N-dimethyl-formamide), the volatiles were removed in vacuo. The residue was dissolved in dichloromethane (2 mL), and the resulting solution was transferred via cannula to a suspension of 4-aminopyridine (113 mg, 1.20 mmol, 5.00 equiv) and triethylamine (270 mL, 1.94 mmol, 8.07 equiv) in dichloromethane (2 mL). After the reaction mixture was stirred for 2.5 h, the volatiles were removed in vacuo. The residue was purified by flash column chromatography (ethyl acetate) to provide the product amide 4—4 as a white solid. $^1$H NMR (400 MHz, CDCl$_3$), δ: 8.50 (br d, 2H, J=6.0 Hz, PyH), 8.11 (br s, 1H, NH), 7.63 (br s, 1H, ArH), 7.58 (m, 3H, ArH and PyH), 6.84 (d, 1H, J=8.4 Hz, ArH), 4.17 (m, 1H, OCHCH$_2$Cy), 2.83 (m, 2H, ArCH$_2$CH$_2$), 2.03 (m, 1H, ArCH$_2$CH$_2$), 1.81 (br d, 1H, J=12.6 Hz, CyH), 1.78–1.54 (m, 6H, CyH, ArCH$_2$CH$_2$, and CH$_2$Cy), 1.42 (m, 1H, CyH), 1.34–1.12 (m, 4H, CyH), 0.96 (m, 2H, CyH); TLC (ethyl acetate), R$_f$ 4—4: 0.21 (UV).

EXAMPLE 5

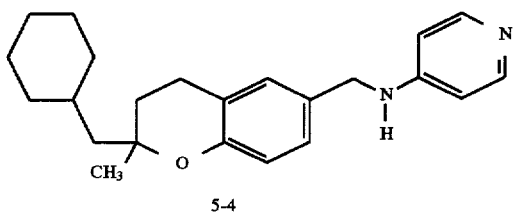

5-4

Compound 4-5

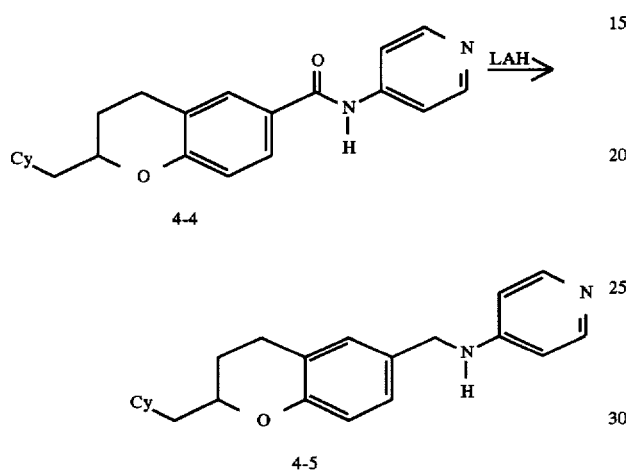

Compound 5-1

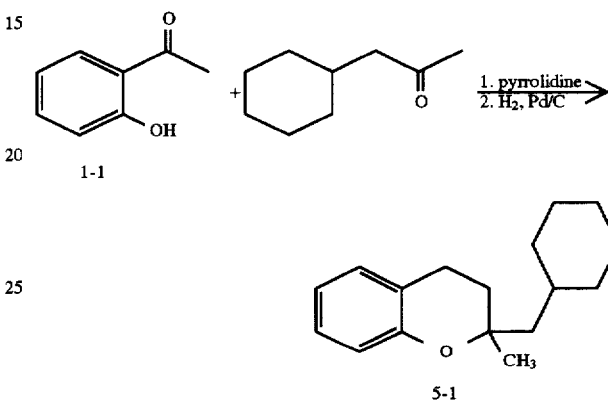

A solution of lithium aluminum hydride in tetrahydrofuran (1.0M, 730 mL, 0.730 mmol, 3.99 equiv) was added to a solution of the amide 4—4 (64 mg, 0.18 mmol, 1 equiv) in tetrahydrofuran (2 mL) at 23° C. The reaction mixture was heated to 50° C. and held at that temperature for 2 h. The mixture was cooled to 0° C., and excess lithium aluminum hydride was quenched by the addition of water (30 mL). Aqueous 15% sodium hydroxide solution (30 mL) and water (90 mL) were added consecutively, and the resulting aluminum salts were removed by filtration and washed with ethyl acetate (50 mL). The filtrate was concentrated and the residue was purified by flash column chromatography (1% methanol in chloroform saturated with ammonia) to afford the amine as a colorless oil. Hydrochloric acid gas was bubbled briefly through a solution of the product amine in ethyl acetate at 23° C. Concentration of the solution provided the pyridinium chloride salt of the product amine, 4–5, as a white solid (mp=188°–190° C.). $^1$H NMR (400 MHz, CDCl$_3$), δ: 8.18 (br d, 2H, J=6.2 Hz, PyH), 7.03 (br d, 1H, J=8.2 Hz, ArH), 7.00 (br s, 1H, ArH), 6.78 (d, 1H J=8.2 Hz, ArH), 6.46 (br d, 2H, J=6.2 Hz, PyH), 4.37 (br s, 1H, NH), 4.22 (d, 2H, J=5.1 Hz, CH$_2$NH), 4.09 (m, 1H, OCHCH$_2$CY), 2.82 (ddd, 1H, J=16.8, 10.8, 5.9 Hz, ArCH$_2$CH$_2$), 2.72 (dt, 1H, J=16.7, 3.8 Hz, ArCH$_2$CH$_2$), 1.98 (m, 1H, ArCH$_2$CH$_2$), 1.82 (br d, 1H, J=12.6 Hz, CyH), 1.78–1.54 (m, 6H, CyH, ArCH$_2$CH$_2$, and CH$_2$Cy), 1.40 (m, 1H, CyH),1.35–1.12 (m, 4H, CyH), 0.96 (m, 2H, CyH); TLC (1% CH$_3$OH-CHCl$_3$ sat'd w/NH$_3$), R$_f$=0.26 (UV).

A solution of 1—1 (1.72 mL, 14.3 mmol, 1.00 equiv), cyclohexylacetone (Lancaster) (2.00 g, 14.3 mmol, 1 equiv), and pyrrolidine (1.20 mL, 14.4 mmol, 1.01 equiv) in anyhydrous methanol (25 mL) was stirred at 23° C. for 1 d. The product mixture was concentrated, and the residue was purified by flash column chromatography (5% ethyl acetate in hexanes initially, then 10% ethyl acetate in hexanes) to provide a mixture (1:1 by $^1$H NMR) of the desired chromanone and starting 2'-hydroxyacetophenone as a colorless oil (1.06 g).

A suspension of the product mixture (1.05 g) and 10% palladium on carbon (1.12 g, 1.05 mmol) in ethanol (20 mL) was heated at 60° C. for 25.5 h. After cooling to 23° C., the solids were removed by filtration through a pad of Celite® and were washed with ethyl acetate (200 mL). The filtrate was concentrated and the residue was purified by flash column chromatography (hexanes) to provide the benzopyran 5-1 product as a colorless oil. $^1$H NMR (400 MHz, CDCl$_3$), δ: 7.07 (br t, 1H, J=7.4 Hz, ArH), 7.04 (br d, 1H, J=7.6 Hz, ArH), 6.80 (td, 1H, J=7.4, 1.2 Hz, ArH), 6.75 (dd, 1H, J=8, 1, 1.0 Hz, ArH), 2.76 (t, 2H, J=6.7 Hz, ArCH$_2$), 1.94–1.38 (m, 8H, CyH and CH$_2$CY), 1.86 (dd, 1H, J=13.6, 6.8 Hz, ArCH$_2$CH$_2$), 1.76 (dd, 1H, J=13.4, 6.6 Hz, ArCH$_2$CH$_2$), 1.30 (s, 3H, CH$_3$), 1.28–0.84 (m, 5H, CyH); TLC (10% ethyl acetate-hexanes), R$_f$=Product benzopyran: 0.63 (UV)

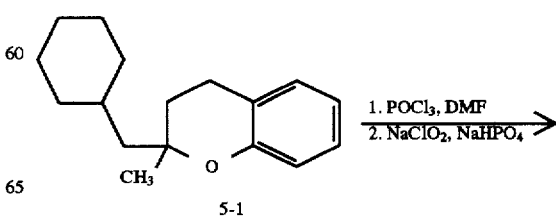

5-1

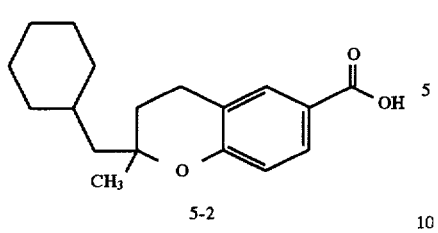

5-2

The formulation of 5-1 and subsequent oxidation of the aldehyde to the carboxylic acid 5-2 were carried out as described in the examples above.

Compound 5-3

For the coupling of the carboxylic acid 5-2 and 4-aminopyridine to give amide 5-3, the following procedure was employed.

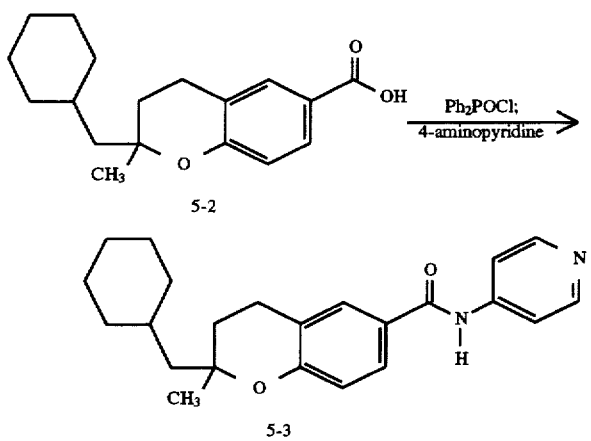

Diphenylphosphinic chloride (62 mL, 0.33 mmol, 1.1 equiv) was added to a solution of the carboxylic acid 5-2 (86 mg, 0.30 mmol, 1 equiv) and triethylamine (50 mL, 0.36 mmol, 1.2 equiv) in tetrahydrofuran (3 mL) at 0° C. After stirring for 30 min at 0° C., 4-aminopyridine (140 mg, 1.49 mmol, 4.97 equiv) was added to the reaction mixture. The resulting mixture was warmed to 23° C. and was stirred at that temperature for 2 h. The product mixture was diluted with ethyl acetate (50 mL) and the resulting solution was washed with aqueous saturated sodium bicarboante solution (2×25 mL) followed by aqueous saturated ammonium chloride solution (2×25 mL). The organic layer was dried over magnesium sulfate and was concentrated to afford the product amide 5-3 as a colorless oil. TLC (ethyl acetate): $R_f$=0.24.

Compound 5-4

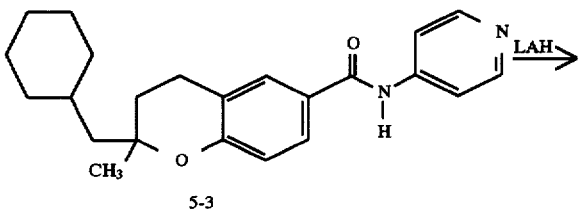

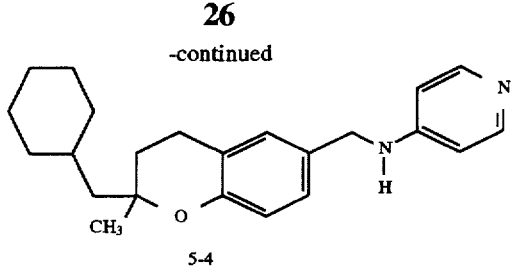

5-4

The reduction of the amide 5-3 to the amine 5-4 was accomplished using lithium aluminum hydride as detailed in the examples above. Amine 5-4: $^1$H NMR (400 MHz, $CDCl_3$), δ: 8.19 (br d, 12H, J=6.2 Hz, PyH), 7.03 (br d, 1H, J=8.2 Hz, ArH), 7.01 (br s, 1H, ArH), 6.74 (d, 1H, J=8.2 Hz, ArH), 6.46 (br d, 1H, J=6.4 Hz, PyH), 4.39 (br s, 1H, NH), 4.22 (d, 1H J=5.3 Hz, $CH_2NH$), 2.74 (t, 2H, J=6.8 Hz, $ArCH_2$), 1.90–1.40 (m, 11H, CyH, $CH_2Cy$, and $ArCH_2CH_2$), 1.30 (s, 3H, $CH_3$), 1.28–0.84 (m, 5H, CyH); Low-Res MS (FAB): Calcd for $C_{23}H_{30}N_2O_1$ $[M+H]^+$: 351; Found: 351; mp: 55°–57° C.; TLC (1% $CH_3OH-CHCl_3$ sat'd w/$NH_3$), $R_f$=0.28 (UV)

EXAMPLE 6

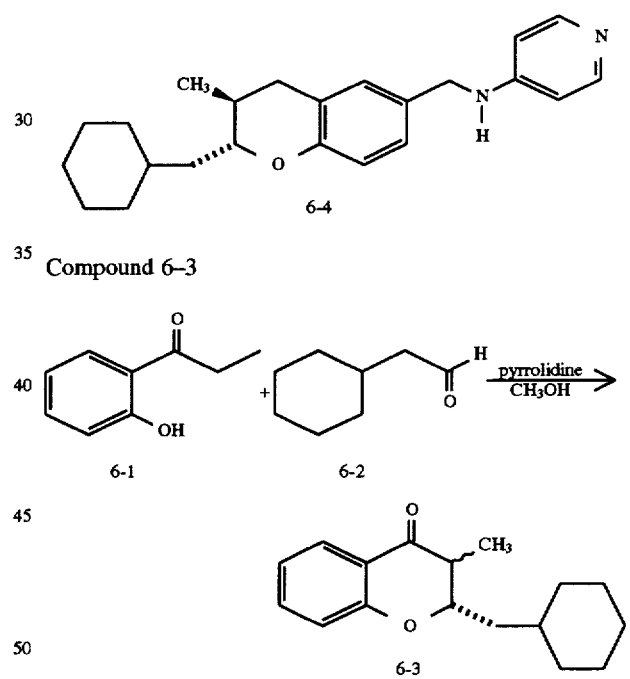

6-4

Compound 6-3

A solution of 2'-hydroxypropiophenone 6-1 (prepared from 1—1 according to the procedure outlined in Tetrahedron Letters (1979) vol. 38, p. 3685) (2.50 g, 16.6 mmol, 1 equiv), cyclohexylacetaldehyde 6-2 (prepared from 2-cyclohexylethanol (Aldrich) using the procedure for preparing heptanal from heptanol outlined in Organic Synthesis, Collective Volume VI, p. 373) (2.50 g, 19.8 mmol, 1.19 equiv), and pyrrolidine (1.40 mL, 16.8 mmol, 1.01 equiv) in anhydrous methanol (200 mL) was stirred at 23° C. for 3 d. The product mixture was concentrated, and the residue was purified by flash column chromatography (5% ethyl acetate in hexanes) to provide separately the trans chromanone 6-3 as a colorless oil (1.05 g, 24%) as well as a 1:1 mixture of cis and trans chromanones 6-3 as a colorless oil. $^1$H NMR trans chromanone:(400 MHz, CDCl$_3$), δ: 7.87 (dd, 1H, J=7.9, 1.6 Hz, ArH), 7.46 (td, 1H, J=7.8, 1.8 Hz, ArH), 6.98 (m, 2H, ArH), 4.24 (td, 1H, J=9.9, 3.1 Hz, ArOCHCH$_2$Cy), 2.57 (m, 1H, ArC(O)CHCH$_3$), 1.84 (br d, 1H, J=12.8 Hz, CyH), 1.79–1.61 (m, 6H, CyH and CH$_2$Cy), 1.53 (m, 1H, CyH), 1.47–1.10 (m, 4H, CyH), 1.22 (d, 3H, J=7.0 Hz, CH$_3$), 1.02 (m, 1H, CyH), 0.90 (m, 1H, CyH); TLC (10% ethyl acetate-hexanes), R$_f$ trans chromanone=0.44 (UV); R$_f$ cis chromanone=0.37 (UV). Compound 6–4

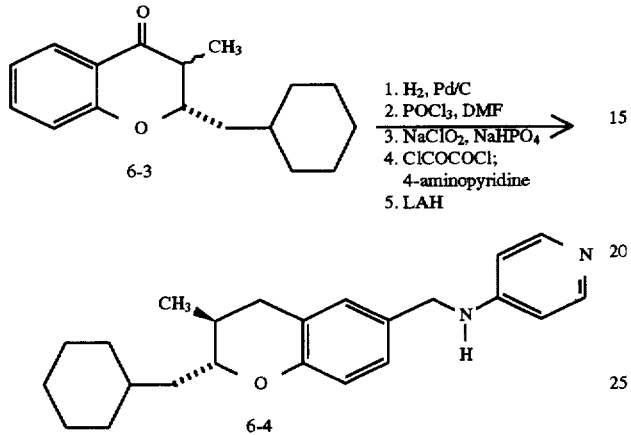

The reduction of trans chromanone 6–3, formulation of the benzopyran ring, oxidation of the resulting aldehyde to the carboxylic acid, coupling of the acid with 4-aminopyridine, and subsequent reduction of the resulting amide to give amine 6–4 were carried out as described above in Example 2 (steps B-F). Amine 6–4: $^1$H NMR (400 MHz, CDCl$_3$), 8.20 (br d, 2H, J=6.3 Hz, PyH), 7.03 (br d, 1H, J=8.3 Hz, ArH), 6.99 (br s, 1H, ArH), 6.80 (d, 1H J=8.3 Hz, ArH), 6.47 (br d, 2H, J=6.4 Hz, PyH), 4.39 (br s, 1H, NH), 4.23 (d, 2H, J=5.1 Hz, CH$_2$NH), 3.80 (td, 1H, J=8.1, 4.4 Hz, OCHCH$_2$Cy), 2.78 (dd, 1H, J=16.4, 5.4 Hz, ArCH$_2$), 2.44 (dd, 1H, J=16.4, 9.3 Hz, ArCH$_2$), 1.85 (m, 2H, CyH and CHCH$_3$), 1.70 (m, 4H, CyH), 1.50 (m, 2H, CH$_2$CY), 1.25 (m, 4H, CyH), 1.02 (d, 3H, J=6.6 Hz, CHCH$_3$), 0.95 (m, 2H, CyH); Low-Res MS (FAB): Calcd for C$_{23}$H$_{31}$N$_2$O$_1$ [M+H]$^+$: 351; Found: 351; mp: 105°–107° C.

EXAMPLE 7

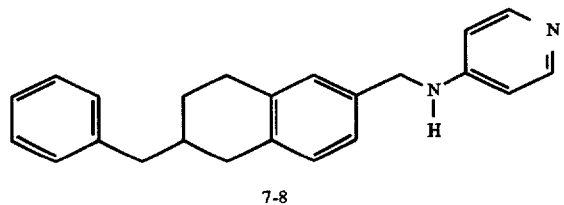

7-8

Compound 7–2

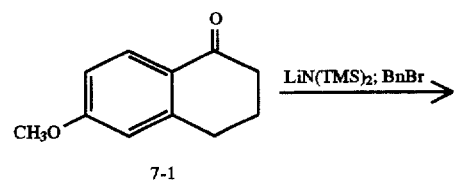

7-1

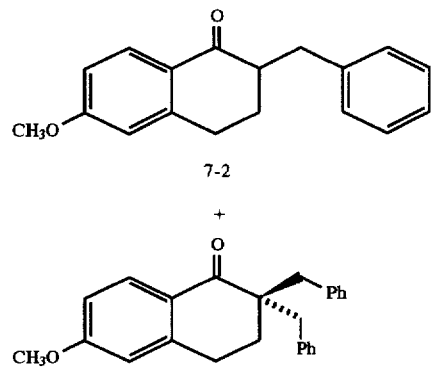

7-2

A solution of potassium hexamethyldisilazide in toluene (0.5M, 60.0 mL, 30.0 mmol, 1.06 equiv) was added to a suspension of 6-methoxytetralone 7–1 (Aldrich) (5.00 g, 28.4 1 equiv) in toluene (25 mL) at –40° C. After stirring for 20 min, the reaction mixture was warmed to 0° C. and held at that temperature for 25 min, then was cooled to –40° C. Benzyl bromide (3.60 mL, 30.3 mmol, 1.07 equiv) was added, and the resulting mixture was warmed to 0° C. and stirred at that temperature for 25 min, then warmed to 23° C. and stirred for 30 min. The product mixture was poured into water (300 mL), and the resulting aqueous mixture was extracted with ethyl acetate (2×100 mL). The combined organic layers were dried over sodium sulfate and were concentrated. The residue was purified by flash column chromatography (20% ethyl acetate in hexanes initially, then 30% ethyl acetate in hexanes) to provide an inseparable mixture of 7–2 and dialkylated product (2.5:1 ratio, respectively, by 1H NMR) as a colorless oil. 1H NMR 7–2 (400 MHz, CDCl$_3$), δ: 8.05 (d, 1H, J=8.8 Hz, ArH), 7.34–7.11 (m, 5H, PhH), 6.84 (dd, 1H, J=8.8, 2.6 Hz, ArH), 6.67 (d, 1H, J=2.4 Hz, ArH), 3.85 (s, 3H, OCH$_3$), 3.50 (dd, 1H, J=13.4, 3.5 Hz, CH$_2$Ph), 2.89 (m, 3H, ArCH$_2$, CH$_2$Ph, and CHCH$_2$Ph), 2.70 (m, 1H, ArCH$_2$), 2.08 (m, 1H, ArCH$_2$CH$_2$), 1.77 (m, 1H, ArCH$_2$CH$_2$); TLC (40% EtOAc-hexanes), R$_f$ 7–2: 0.58 (UV).

Compound 7–3

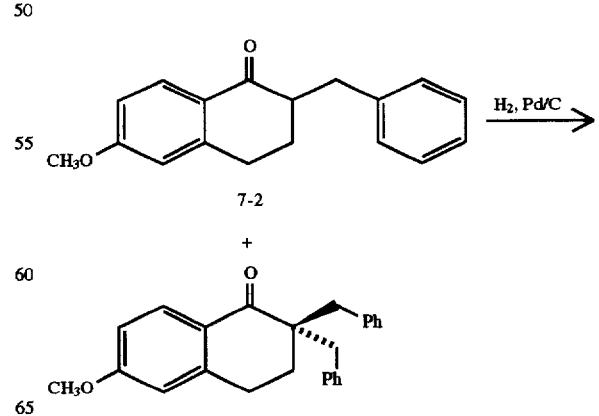

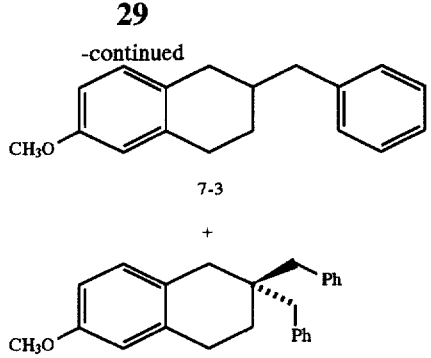

A suspension of 7-2 and corresponding dialkylated impurity and 10% palladium on carbon (1.0 g, 0.940 mmol, 0.047 equiv) was heated at 70° C. under a hydrogen balloon for 16 h. Acetic acid was added (15 mL) followed by 10% palladium on carbon (1.0 g, 0.940 mmol, 0.070 equiv). The mixture was further heated at 70° C. under a hydrogen balloon for 5 h. After cooling to 23° C., the solids were removed by filtration through a pad of Celite® and were washed with ethyl acetate (200 mL). The filtrate was concentrated and the residue was purified by flash column chromatography (1% ethyl acetate in hexanes initially, then 3% ethyl acetate in hexanes) to provide an inseparable mixture of tetrahydronapthalene 7-3 and corresponding impurity (2.5:1 ratio, respectively, by 1H NMR) as a colorless oil. $^1$H NMR 7-3 (400 MHz, CDCl$_3$), δ: 7.33–7.18 (m, 5H, PhH), 6.93 (d, 1H, J=8.4 Hz, ArH), 6.66 (dd, 1H, J=8.4, 2.6 Hz, ArH), 6.61 (d, 1H, J=2.6 Hz, ArH), 3.76 (s, 3H, OCH$_3$), 2.76 (m, 3H, ArCH$_2$ and CH$_2$Ph), 2.66 (d, 2H, J=7.1 Hz, CH$_2$Ph), 2.40 (br dd, 1H, J=15.8, 10.5 Hz, ArCH$_2$), 2.02 (m, 1H, ArCH$_2$CHCH$_2$Ph), 1.91 (m, 1H, ArCH$_2$CH$_2$), 1.42 (m, 1H, ArCH$_2$CH$_2$); TLC (10% EtOAc-hexanes), R$_f$ 7-3: 0.40 (UV).

Compound 7-4

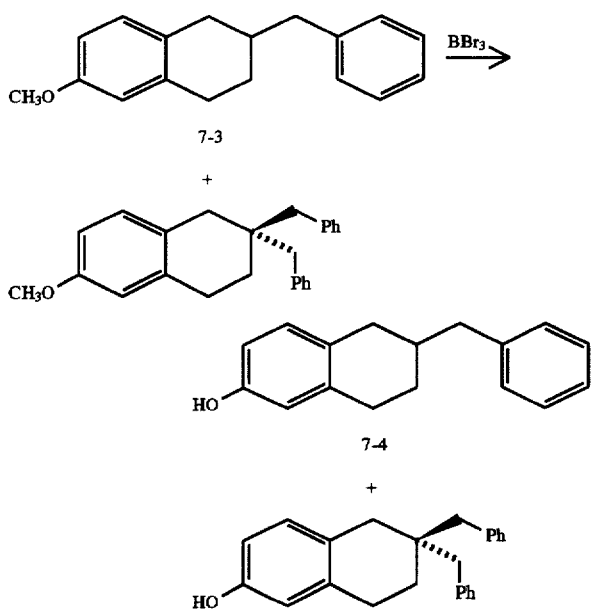

A solution of boron tribromide in dichloromethane (1.0M, 7.0 mL, 7.0 mmol, 1.3 equiv) was added to a solution of the mixture of tetrahydronaphthalene 7-3 and corresponding impurity (2.5:1, respectively, by $^1$H NMR, 1.50 g, 5.39 mmol of tetrahydrophthalene mixture, 3.85 mmol of 7-3 based on $^1$H NMR ratio, 1 equiv) in dichloromethane (50 mL) at −78° C. The reaction mixture was warmed to 0° C. and held at that temperature for 1 h. The product mixture was poured into water (200 mL), and the resulting biphasic mixture was extracted with dichloromethane (2×100 mL). The combined organic layers were dried over sodium sulfate and were concentrated to leave an inseparable mixture of phenol 7-4 and corresponding impurity (2.5:1 ratio, respectively, by 1H NMR) as a brown oil. TLC (20% EtOAc-hexanes), R$_f$ 7-4: 0.21; R$_f$ 7-3: 0.53.

Compound 7-5

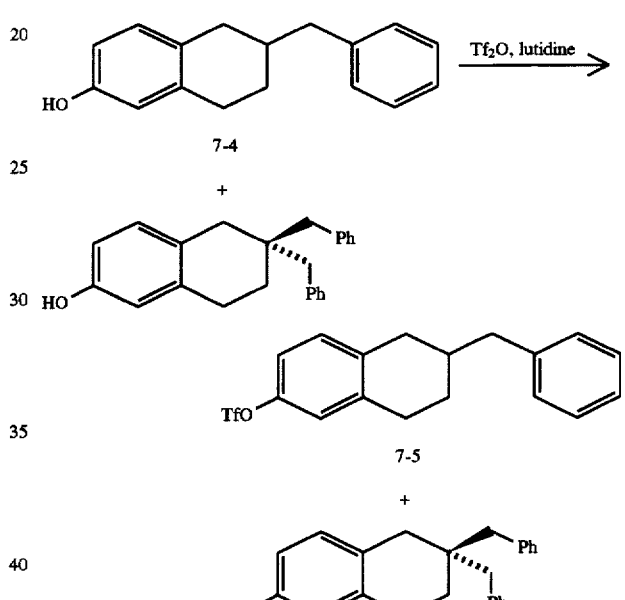

Trifluormethanesulfonic anhydride (1.2 mL, 7.1 mmol, 1.3 equiv) was added to a solution of phenol 7-4 and corresponding impurity (5.39 mmol of phenol mixture, 3.85 mmol of 7-4 based on 2.5:1 $^1$H NMR ratio, 1 equiv) and 2,6-lutidine (900 mL, 7.7 mmol, 1.4 equiv) in dichloromethane (50 mL) at −78° C. The reaction mixture was warmed to 0° C. and held at that temperature for 1 h. The product mixture was poured into aqueous saturated sodium bicarbonate solution (150 mL). The biphasic mixture was extracted with dichloromethane (2×100 mL). The combined organic layers were dried over sodium sulfate and were concentrated. The residue was purified by flash column chromatography (5% ethyl acetate in hexanes) to provide an inseparable mixture of triflate 7-5 and corresponding impurity (2.5:1 $^1$H NMR ratio, respectively, by 1H NMR) as a colorless oil. TLC (10% EtOAc-hexanes), R$_f$ 7-5: 0.41; R$_f$ 7-4: 0.09.

Compound 7-6

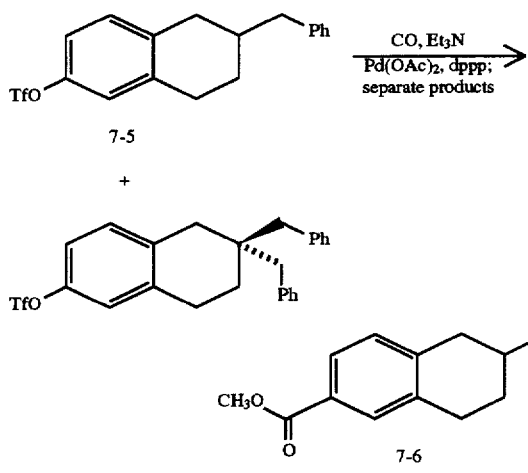

Carbon monoxide gas was bubbled through a deoxygenated solution of triflates 7-5 and corresponding impurity (2.5:1 $^1$H NMR ratio, 860 mg, 2.17 mmol of triflate mixture, 1.55 mmol of triflate 7-5 based on $^1$H NMR ratio, 1 equiv), triethylamine (1.0 mL, 7.2 mmol, 3.3 equiv), 1,3-bis(diphenylphosphino)propane (55 mg, 0.13 mmol, 0.060 equiv) and palladium(II) acetate (30 mg, 0.13 mmol, 0.060 equiv) in a mixture of methanol (10 mL) and dimethylsulfoxide (5 mL) at 23° C. for 5 min. The reaction mixture was heated at 80° C. under a carbon monoxide balloon for 3 h. 1,3-Bis (diphenylphosphino)propane (55 mg, 0.13 mmol, 0.060 equiv) and palladium(II) acetate (30 mg, 0.13 mol, 0.060 equiv) were then added to the reaction mixture and heating was continued for 3 h. The reaction mixture was allowed to cool, then diluted with water (200 mL). The resulting aqueous mixture was extracted with a 1:1 mixture of ethyl acetate and hexanes (2×100 mL). The combined organic layers were dried over sodium sulfate and were concentrated. The residue was purified by flash column chromatography (5% ethyl acetate in hexanes) to afford separately the methyl ester 7-6 as a colorless oil as well as the undesired dibenzylated methyl ester impurity as a colorless oil. 1H NMR 7-6 (400 MHz, CDCl$_3$), δ: 7.75 (br s, 1H, ArH), 7.72 (br d, 1H, J=8.1 Hz, ArH), 7.33–7.17 (m, 5H, PhH), 7.06 (d, 1H, J=7.9 Hz ArH), 3.87 (s, 3H, OCH$_3$), 2.82 (m, 3H, ArCH$_2$ and CH$_2$Ph), 2.66 (d, 2H, J=7.1 Hz, CH$_2$Ph), 2.48 (br dd, 1H, J=17.0, 10.4 Hz, ArCH$_2$), 2.04 (m, 1H, ArCH$_2$CHCH$_2$Ph), 1.95 (m, 1H, ArCH$_2$CH$_2$), 1.44 (m, 1H, ArCH$_2$CH$_2$); TLC (10% EtOAc-hexanes), R$_f$ 7-6=0.28 (UV).

Compound 7-7

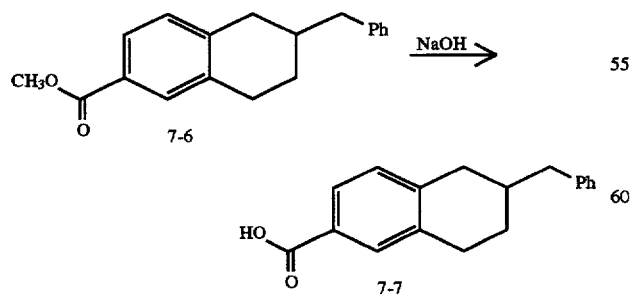

A solution of the ester 7-6 (195 mg, 0.696 mmol, 1 equiv) in a mixture of tert-butanol (6 mL), water (2 mL), and aqueous sodium hydroxide solution (1 N, 4 mL, 4 mmol, 6 equiv) was heated at 75° C. for 2 h. The product mixture was allowed to cool to 23° C., then was diluted with aqueous 10% potassium hydrogen sulfate solution (100 mL). The aqueous mixture was extracted with ethyl acetate (2×100 mL). The combined organic layers were dried over sodium sulfate and were concentrated to provide the carboxylic acid 7—7 as a white solid.

Compound 7-8

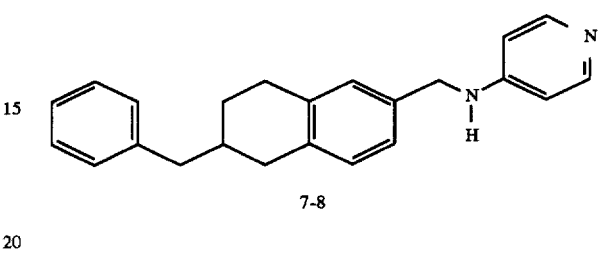

The coupling of the carboxylic acid 7—7 and 4-aminopyridine and subsequent reduction of the amide were accomplished as described in the benzopyran series to yield 7-8. $^1$H NMR (400 MHz, CDCl$_3$), δ: 8.18 (br d, 2H, J=6.2 Hz, PyH), 7.34–7.16 (m, 5H, PhH), 7.02 (br m, 3H, ArH), 6.45 (br d, 2H, J=6.4 Hz, PyH), 4.42 (br s, 1H, NH), 4.26 (d, 2H, J=5.3 Hz, CH$_2$NH), 2.79 (m, 3H, ArCH$_2$), 2.67 (d, 2H, J=7.1 Hz, CH$_2$Ph), 2.46 (dd, 1H, J=16.3, 10.6 Hz, ArH), 2.05 (m, 1H, ArCH$_2$CHCH$_2$Ph), 1.95 (m, 1H, ArCH$_2$CH$_2$), 1.44 (m, 1H, ArCH$_2$CH$_2$); Low-Res MS (FAB): Calcd for C$_{23}$H$_{25}$N$_2$ [M+H]$^+$: 329 Found: 329; TLC (1% CH$_3$OH-CHCl$_3$ sat'd w/NH3), R$_f$ 0.31 (UV).

EXAMPLE 8

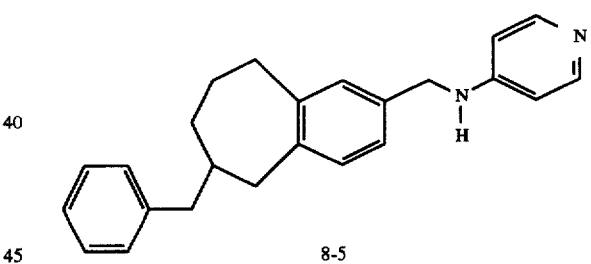

Compound 8-2

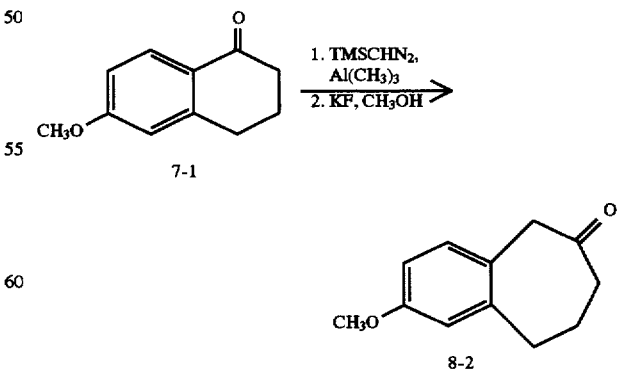

A solution of trimethylaluminum in hexanes (2.0M, 6.20 mL, 12.4 mmol, 1.00 equiv) was added to a solution of 6-methoxy-tetralone 7-1 (2.18 g, 12.4 mmol, 1 equiv) in dichloromethane (25 mL) at −10° C. (ice-salt bath). After the reaction mixture was stirred at −10° C. for 15 min, a solution of (trimethylsilyl)diazomethane in hexanes (2.0 M, 7.0 mL, 14.0 mmol, 1.13 equiv) was added. The reaction mixture was stirred for 1 h, then allowed to warm to 23° C. and stirred for 2.5 h. The product mixture was poured into water (200 mL) and the resulting biphasic mixture was extracted with dichloromethane (2×100 mL). The combined organic layers were dried over sodium sulfate and were concentrated. The residue was purified by flash column chromatography (5% ethyl acetate in hexanes) to afford mostly the desired silyl enol ether product as a colorless oil. TLC (10% EtOAc-hexanes): silyl enol ether R$_f$=0.64; starting tetralone R$_f$=0.36.

Excess 50 wt. % potassium fluoride on Celite® (5 g) was added to a solution of the enol silyl ether in methanol (50 mL) at 23° C., and the resulting mixture was stirred for 1 h. The solids were removed by filtration and washed with methanol (50 mL). The filtrate was concentrated, and the residue purified by flash column chromatography (20% ethyl acetate in hexanes) to provide the desired ketone 8-2 as a colorless oil. $^1$H NMR (300 MHz, CDCl$_3$). δ: 7.07 (d, 1H, J=8.2 Hz, ArH), 6.72 (d, 1H, J=2.4 Hz, ArH), 6.70 (dd, 1H, J=8.2, 2.4 Hz, ArH), 3.80 (s, 3H, OCH$_3$), 3.65 (s, 2H, ArCH$_2$C(O)), 2.91 (m, 2H, ArCH$_2$), 2.55 (t, 2H, J=7.2 Hz, ArCH$_2$C(O)CH$_2$), 2.00 (m, 2H, ArCH$_2$CH$_2$); TLC (20% EtOAc-hexanes). Product ketone: R$_f$=0.23 (UV).

Compound 8-3

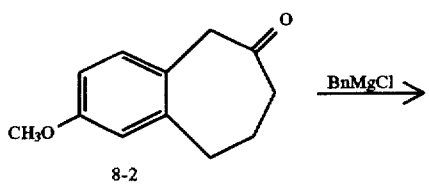

A solution of benzylmagnesium chloride in tetrahydrofuran (2.0M, 3.0 mL, 6.0 mmol, 3.8 equiv) was added to a solution of the ketone 8-2 (300 mg, 1.58 mmol, 1 equiv) in tetrahydrofuran (8 mL) at 0° C. The reaction mixture was stirred at 0° C. for 1 h, then diluted with aqueous pH 7 phosphate buffer solution (200 mL). The aqueous mixture was extracted with a 1:1 mixture of ethyl acetate and hexanes (2×100 mL). The combined organic layers were dried over sodium sulfate and were concentrated. The residue was purified by flash column chromatography (20% ethyl acetate in hexanes) to provide the addition product 8-3 as a colorless oil. $^1$H NMR (300 MHz, CDCl$_3$). δ: 7.33-7.19 (m, 5H, PhH), 7.00 (d, 1H, J=8.1 Hz, ArH), 6.67 (d, 1H, J=2.4 Hz, ArH), 6.65 (dd, 1H, J=8.1, 2.7 Hz, ArH), 3.78 (s, 3H, OCH$_3$), 2.92 (m, 2H, CH$_2$Ph), 2.73 (m, 4H, ArCH$_2$), 1.75 (m, 4H, ArCH$_2$CH$_2$ and ArCH$_2$CH$_2$CH$_2$); TLC (40% EtOAc-hexanes). Addition product: R$_f$=0.54 (UV).

Compound 8-4

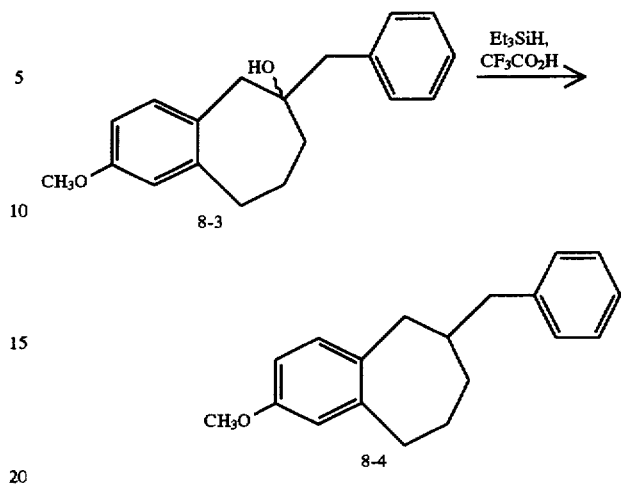

Trifluoroacetic acid (4 mL, excess) was added to a solution of the alcohol 8-3 (390 mg, 1.38 mmol, 1 equiv) and triethylsilane (500 mL, 3.13 mmol, 2.27 equiv) in dichloromethane (10 mL) at 23° C. The reaction mixture was stirred at 23° C. for 16 h, then was concentrated. The residue was purified by flash column chromatography (100% hexanes initially, then 3% ethyl acetate in hexanes) to provide the reduced product 8-4 as a colorless oil. $^1$H NMR (300 MHz, CDCl$_3$). δ: 7.33-7.12 (m, 5H, PhH), 6.88 (d, 1H, J=8.2 Hz, ArH), 6.66 (d, 1H, J=2.8 Hz, ArH), 6.59 (dd, 1H, J=8.2, 2.7 Hz, ArH), 3.77 (s, 3H, OCH$_3$), 2.83-2.62 (m, 4H, ArH), 2.59 (dd, 1H, J=13.6, 7.3 Hz, CH$_2$Ph), 2.50 (dd, 1H, J=13.6, 7.5 Hz, CH$_2$Ph), 1.86 (m, 3H, ArCH$_2$CH$_2$ and ArCH$_2$CHCH$_2$Ph), 1.47 (m, 2H, ArCH$_2$CH$_2$CH$_2$); TLC (20% EtOAc-hexanes). Reduced product: R$_f$=0.55 (UV).

Compound 8-5

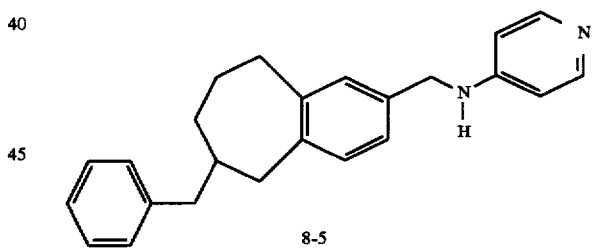

The remaining steps of the sequence, demethylation of the methyl ether, conversion of the resulting alcohol to its corresponding triflate, carbonylation of the triflate, saponification of the product methyl ester, coupling of the carboxylic acid and 4-amino pyridine, and the reduction of the amide to product 8-5 were carried out as described in the example above. $^1$H NMR (400 MHz, CDCl$_3$). δ: 0.19 (br d, 2H, J=6.4 Hz, PyH), 7.33-7.11 (m, 5H, PhH), 7.04 (br s, 1H, ArH), 7.02 (dd, 1H, J=7.8, 1.7 Hz, ArH), 6.95 (d, 1H, J=7.8 Hz, ArH), 6.46 (br d, 2H, J=6.2 Hz, PyH), 4.47 (br s, 1H, NH), 4.28 (d, 2H, J=5.5 Hz, CH$_2$NH), 2.87-2.65 (m, 4H, ArCH$_2$), 2.60 (dd, 1H, J=13.7, 7.5 Hz, CH$_2$Ph), 2.53 (dd, 1H, J=17.5, 7.3 Hz, CH$_2$Ph), 1.89 (m, 3H, ArCH$_2$CHCH$_2$Ph and ArCH$_2$CH$_2$), 1.47 (m, 2H, ArCH$_2$CH$_2$CH$_2$); Low-Res MS (FAB): Calcd for C$_{24}$H27N$_2$ [M+H]+: 343, Found: 343; TLC (1% CH$_3$OH-CHCl$_3$ sat'd w/NH$_3$), Product R$_f$=0.12 (UV).

Additional compounds within the scope of the present invention are shown below:

TABLE 1

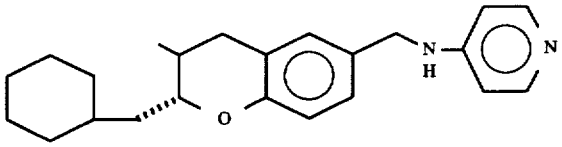

| R¹ | R² | X | n |
|---|---|---|---|
| PhCH$_2$— | H | CH$_2$ | 1 |
| PhCH$_2$— | H | CH$_2$ | 2 |
| Ph | H | O | 1 |
| 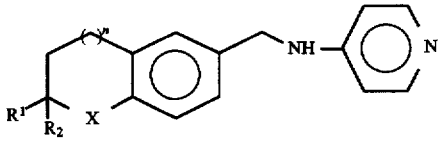 | CH$_3$ | O | 1 |
| 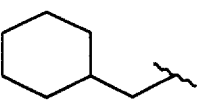 | H | O | 1 |
| PhCH$_2$— | H | O | 1 |
|  | H | O | 1 |

TABLE 2

Compounds

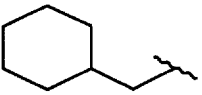

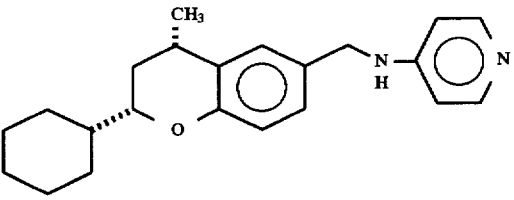

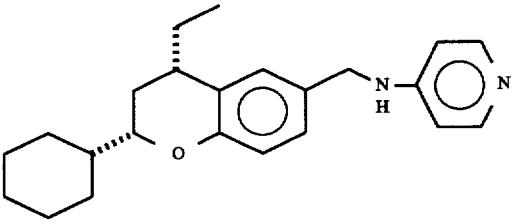

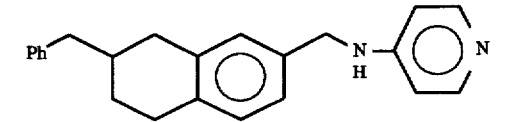

TABLE 2-continued

Compounds

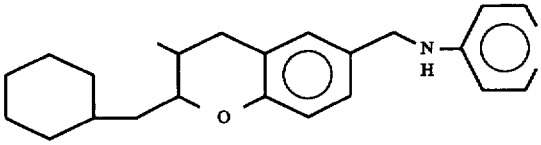

Compounds listed in tables 1 and 2 inhibited human thrombin with Ki's in the range of 90 to 4000 nM as determined by the assay outlined below.

In vitro assay for determining proteinase inhibition

Assays of human a-thrombin and human trypsin were performed at 25° C. in 0.05M TRIS buffer pH 7.4, 0.15M NaCl, 0.1% PEG. Trypsin assays also contained 1 mM CaCl$_2$.

In assays wherein rates of hydrolysis of a p-nitroanilide (pna) substrate were determined, a Thermomax 96-well plate reader was used to measure (at 405 nm) the time dependent appearance of p-nitroaniline. sar-PR-pna (sarcosine-Pro-Arg-p-nitroanilide) was used to assay human a-thrombin ($K_m$=125 µM) and human trypsin ($K_m$=59 µM). p-Nitroanilide substrate concentration was determined from measurements of absorbance at 342 nm using an extinction coefficient of 8270 cm$^{-1}$M$^{-1}$.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate Z-GPR-afc (Cbz-Gly-Pro-Arg-7-amino-4-trifluoromethyl coumarin) ($K_m$=27 µM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration 0.5 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m$/[S], [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in equation 1.

$$V_o/V_i = 1 + [I]/K_i \tag{1}$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

Thrombin Inhibitors—Therapeutic Uses

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, thrombin inhibitors can be added to or contacted with any medium containing or suspected of containing thrombin and in which it is desired that blood coagulation be inhibited, e.g. when contacting the mammal's blood with material selected from the group consisting of vascular grafts, stents, orthopedic prothesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.1 mg per kg of body weight per day (mg/kg/day) to about 100 mg/kg/day and preferably 1.0–100 mg/kg/day and most preferably 1–20 mg/kg/day. Intravenously, the most preferred doses will range from about 0.01 to about 10 mg/kg/minute during a constant rate infusion. Advantageously, the thrombin inhibitors may be administered in divided doses of two, three, or four times daily. Furthermore, they can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

For example, oral tablets can be prepared which contain an amount of active compound of between 100 and 500 mg, e.g. 100, 200, 300, 400 or 500 mg. Typically, a patient in need of thrombin inhibitor compound, depending on weight and metabolism of the patient, would be administered between about 100 and 1000 mg active compound per day. For a patient requiring 1000 mg per day, two tablets containing 250 mg of active compound can be administered in the morning and two tablets containing 250 mg of active compound can again be administered in the evening. For a patient requiring 500 mg per day, one tablet containing 250 mg of active compound can be administered in the morning and one tablet containing 250 mg of active compound can again be administered in the evening.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or betalactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The thrombin inhibitors can also be co-administered with suitable anti-coagulation agents or thrombolytic agents such as plasminogen activators or streptokinase to achieve synergistic effects in the treatment of various ascular pathologies. For example, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter. They may also be combined with heparin, aspirin, or warfarin.

EXAMPLE 9

Tablet Preparation

Tablets containing 100.0, 200.0, and 300.0 mg, respectively, of 1,2,3,4-tetrahydro-2(RS)-cyclohexyl-6-(4'-amino-pyridyl)methyl-benzopyran are prepared as illustrated below:

| Ingredient | Amount-mg | | |
|---|---|---|---|
| 1,2,3,4-tetrahydro-2(RS)-cyclohexyl-6-(4'-amino-pyridyl)methyl-benzopyran | 100.0 | 200.0 | 300.0 |
| Microcrystalline cellulose | 160.0 | 150.0 | 200.0 |
| Modified food corn starch | 20.0 | 15.0 | 10.0 |
| Magnesium stearate | 1.5 | 1.0 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 100.0, 200.0, and 300.0 mg, respectively, of active ingredient per tablet.

EXAMPLE 10

An intravenous dosage form of the above-indicated active compound is prepared as follows:

| 1,2,3,4-tetrahydro-2(RS)-cyclohexyl-6-(4'-amino-pyridyl)methyl-benzopyran | 0.5–10.0 mg |
|---|---|
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

What is claimed is:

1. Compounds of the invention have the following structure:

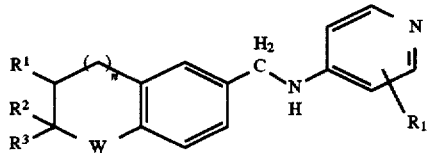

wherein
n=0, 1 or 2;
W=O, NH, or CH$_2$;
R$^1$=H,
C$_{1-4}$ lower alkyl,
C$_{2-4}$ lower alkenyl,
C$_{2-4}$ lower alkynyl;
R$^2$=
—(CH$_2$)$_m$C$_6$H$_5$, or
—(CH$_2$)$_m$C$_6$H$_{11}$,
where m=0, 1 or 2; and
R$^3$=H,
C$_{1-4}$ lower alkyl,
C$_{2-4}$ lower alkenyl,
C$_{2-4}$ lower alkynyl;
and pharmaceutically acceptable salts thereof.

2. A compound of claim 1 having the formula:

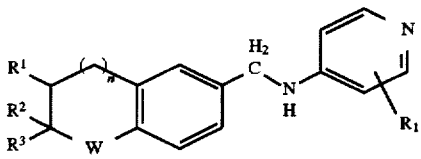

wherein
n=1 or 2;
W=O or CH$_2$;
R$^1$=H or CH$_3$;
R$^2$=
—C$_6$H$_5$,
—C$_6$H$_{11}$,
—CH$_2$C$_6$H$_5$, or
—CH$_2$C$_6$H$_{11}$; and
R$^3$=H or CH$_3$, and pharmaceutically acceptable salts thereof.

3. A compound of claim 2 which has the structure:

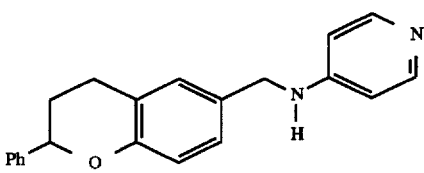

,

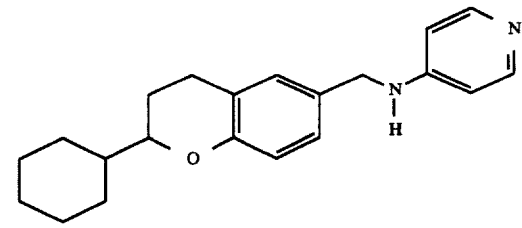

,

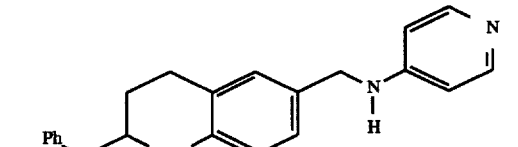

,

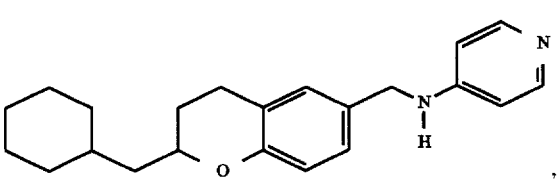

,

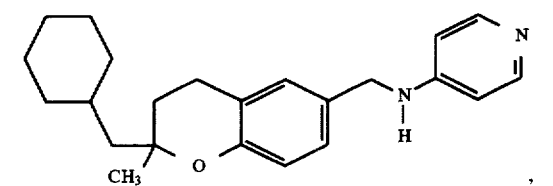

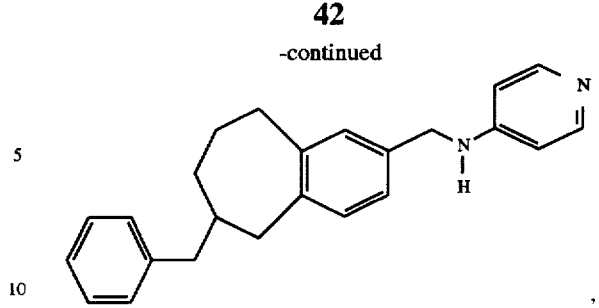

and pharmaceutically acceptable salts thereof.

4. A composition for inhibiting thrombin in blood comprising a compound of claim 1 and a pharmaceutically acceptable carrier.

5. A method for inhibiting thrombin in blood in a mammal comprising administering to the mammal a composition of claim 4.

6. A method for inhibiting formation of blood platelet aggregates in blood in a mammal comprising administering to the mammal a composition of claim 4.

7. A method for inhibiting formation of fibrin in blood in a mammal comprising administering to the mammal a composition of claim 4.

8. A method for inhibiting thrombus formation in blood in a mammal comprising administering to the mammal a composition of claim 4.

* * * * *

UNITED STATES PATENT AND TRADEMARK OFFICE
CERTIFICATE OF CORRRECTION

Page 1 of 2

PATENT NO. : 5,792,761
DATED : Aug. 11, 1998
INVENTOR(S) : Fraley et al.

It is certified that error appears in the above-identified patent and that said Letters Patent is hereby corrected as shown below:

Title page, item [56] insert the following:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 5 | 3 | 9 | 9 | 5 | 6 | 4 | 3/21/95 | HACKLER ET AL. | | | |
| | | 5 | 5 | 1 | 8 | 7 | 3 | 5 | 5/21/96 | STURZEBECHER ET AL. | | | |
| | | | | | | | | | | | | |

UNITED STATES PATENT AND TRADEMARK OFFICE
CERTIFICATE OF CORRRECTION

PATENT NO. : 5,792,761
DATED : Aug. 11, 1998
INVENTOR(S) : Fraley et al.

Page 2 of 2

It is certified that error appears in the above-identified patent and that said Letters Patent is hereby corrected as shown below:

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | WO | 92/ | 0 | 2 | 5 | 0 | 2 | 2/20/92 | PCT | | | | |
| | WO | 96/ | 1 | 0 | 9 | 9 | 9 | 4/18/96 | PCT | | | | |
| | | 5 | 8 | 7 | 4 | 9 | 9 A1 | 3/16/94 | EPO | | | | |
| | | | | | | | | | | | | | |

Signed and Sealed this

Thirteenth Day of April, 1999

Attest:

Q. TODD DICKINSON

*Attesting Officer*   *Acting Commissioner of Patents and Trademarks*